(12) United States Patent
McKerracher et al.

(10) Patent No.: US 7,169,783 B2
(45) Date of Patent: Jan. 30, 2007

(54) (+)-TRANS-4-(1-AMINOETHYL)-1-(4-PYRIDYCARBAMOYL)-CYCLOHEXANE AND METHOD FOR PROMOTING NEURAL GROWTH IN THE CENTRAL NERVOUS SYSTEM AND IN A PATIENT AT A SITE OF NEURONAL LESION

(75) Inventors: Lisa McKerracher, Montreal (CA); Maxime Lehmann, Marseille (FR)

(73) Assignee: Universite de Montreal (CA)

( * ) Notice: Subject to any disclaimer, the term of this patent is extended or adjusted under 35 U.S.C. 154(b) by 38 days.

(21) Appl. No.: 10/022,301

(22) Filed: Dec. 17, 2001

(65) Prior Publication Data

US 2002/0119140 A1     Aug. 29, 2002

Related U.S. Application Data

(63) Continuation-in-part of application No. 09/184,572, filed on Nov. 2, 1998.

(51) Int. Cl.
*A61K 31/535*    (2006.01)
*A61F 2/00*       (2006.01)

(52) U.S. Cl. .................................. 514/238.2; 424/423
(58) Field of Classification Search ...................... 514/2
See application file for complete search history.

(56) References Cited

U.S. PATENT DOCUMENTS

| | | | |
|---|---|---|---|
| 4,997,834 | A | 3/1991 | Muro et al. |
| 5,134,121 | A | 7/1992 | Obley et al. |
| 5,543,498 | A | 8/1996 | Fishman et al. |
| 5,645,829 | A | 7/1997 | Shockley et al. |
| 5,661,033 | A | 8/1997 | Ho et al. |
| 5,672,344 | A | 9/1997 | Kelley et al. |
| 5,851,786 | A | 12/1998 | Johnson et al. |
| 6,180,597 | B1 | 1/2001 | Liao et al. |
| 6,218,410 | B1 | 4/2001 | Uehata et al. |
| 6,451,825 | B1 | 9/2002 | Uehata et al. |

FOREIGN PATENT DOCUMENTS

| | | |
|---|---|---|
| CA | 2263425 | 2/1998 |
| EP | 0 370 498 A3 | 5/1990 |
| WO | WO 97/18303 | 5/1997 |
| WO | WO 98/46754 | 10/1998 |
| WO | WO 99/08533 | 2/1999 |

OTHER PUBLICATIONS

Sylvani et al., Pediatric Neurology, 10(3):228-32, 1994.*
Eberlein et al., Br. J. Pharmacol., 133:1172-1180, 2001.*
Varon et al., J. of Neurotrauma 11(5):473-486, 1994.*
Takahashi et al., Biochem. & Biophys. Res. Communications, 190(3):1156-62, 1993.*
Caporale et al., PNAS 92:75-82, 1995.*
Jalink et al. (1994) J. of Cell Biol. 126(3):801-810.
Li et al. PNAS (1980) 77(6):3211-3214.
McKerracher et al. (1999) Exp. Opin. Ther. Patents 9(11):1571-1574.
Jackowski, (1995) Br. J. of Neurosurgery 9:303-317.
Zalish et al. (1993) Retina 13:145-147.
Bartsch et al. (1995) Neuron 15:1375-1381.
Amano et al. (1997) Science 275:1308-1311.
Chardin et al. (1988) Nucleic Acids Research 16:2717.
Diekmann et al. (1995) Methods in Enzymology 256:207-215.
Dillon et al. (1995) Methods in Enzymology 256:174-195.
Hall (1994) Annu. Rev. Cell Biol. 10:31-54.
Hutchens et al. (1997) Molecular Biology of the Cell 8:481-500.
Ishizaki et al. (1997) FEBS Letters 404:118-124.
Jin et al. (1997) J. Neurosci. 17(16):6256-6263.
Katoh et al. (1998) J. Biol. Chem. 273(5):2489-2492.
Laudanna et al. (1996) Science 271:981-983.
Luo et al. (1996) Nature 379:837-840.
Luo et al. (1994) Genes & Development 8:1787-1802.
Matsui et al. (1996) The EMBO Journal 15(9):2208-2216.
Morii et al. (1995) Methods in Enzymology 256:196-206.
Nobes et al. (1995) Cell 81:53-62.
Somlyo (1997) Nature 389:908-911.
Song et al. (1998) Science 281:1515-1518.
Tigyi et al. (1996) Journal of Neurochemistry 66(2):537-548.
Udagawa et al. (1996) J. Biol. Chem. 271(21):12542-12548.
Uehata et al. (1997) Nature 389:990-994.
Van Leeuwen et al. (1997) J. Cell. Biol. 139(3):797-807.
Yermian et al. (1987) Nucleic Acids Research 15(4):1869.
Zipkin et al. (1997) Cell 90:883-894.
Chuang et al. (1993) "GDP Dissociation Inhibitor Prevents Intrinsic and GTPase Activating Protein-stimulated GTP Hydrolysis by the Rac GTP-binding Protein", J. of Biol. Chem. 268(2):775-778.
Crutcher et al. (1986) "The Role of Growth Factors in Neuronal Development and Plasticity", CRC Crit. Rev. in Neurobiol. 2(3):297-333.
Lamoureaux et al. (1997) "Rac is required for growth cone function but not neurite assembly", J. of Cell Science 110:635-641.
Luo et al. (1997) "Rho family small GTP-binding proteins in growth cone signalling", Current Opinion in Neurobiology 7:81-86.
Malosio et al. (1997) "Differential Expression of Distinct Memebers of Rho Family GTP-Binding Proteins . . . Family", J. of Neuroscience 17(17):6717-6728.

(Continued)

Primary Examiner—Sharon Turner
(74) Attorney, Agent, or Firm—Fish & Richardson P.C.

(57) ABSTRACT

The invention relates to an antagonist of one or more of Rho family members having ability to elicit neurite outgrowth from cultured neurons in an assay method which includes culturing neurons on a substrate that incorporates a growth-inhibiting amount of Rho family member and exposing the cultured neurons to a candidate Rho family member antagonist agent to permit neuron growth. Candidates which elicit neurite outgrowth from the cultured neurons are thus identified as Rho family antagonists.

8 Claims, 12 Drawing Sheets

OTHER PUBLICATIONS

Nishiki et al. (1990) "ADP-Ribosylation of the *rho/rac* Proteins Induces Growth Inhibition, . . . Cultured PC-12 Cells". Biochem. And Biophys. Res. Comm. 167(1):265-272.

Schwab et al. (1993) "Inhibitors of Neurite Growth", Ann. Rev. of Neurosci. 16:565-595.

Kozma et al. (1997) "Rho family GTPases and neuronal growth cone remodelling: Relationship between . . . acid", Molecular and Cellular Biology 17(3):1201-1211.

Martin F.B.G. Gebbink et al. (1997) "Identification of a novel, putative rho-specific GDP/GTP exhange factor and a rhoA-binding protein: control of neuronal morphology", J. of Cell Biology 137(7):1603-1613.

Nikolic et al. (1998) "The p35/Cdk5 kinase is a neuron-specific Rac effector that inhibits Pak1 activity", Nature 395:194-198.

Bartsch et al., "Lack of Evidence That Myelin-Associated Glycoprotein Is a Major Inhibitor of Axonal Regeneration in the CNS", Neuron, 15:1375-1381 (1995).

Barinaga, "Old Protein Provides New Clue To Nerve Regeneration Puzzle", Science, New Series, 265(5180):1800-1801 (1994).

Braun et al., "Laminin Overrides the Inhibitory Effects of Peripheral Nervous System and Central Nervous System Myelin-Derived Inhibitors of Neurite Growth" J. Neurosci. Res., 42:594-602 (1995).

Caroni et al., "Antibody against Myelin-Associated Inhibitor of Neurite Growth Neutralizes Nonpermissive Substrate Properties of CNS White Matter", Neuron, 1(1):85-96 (1988).

Caroni et al., "Two Membrane Protein Fractions from Rat Central Myelin with Inhibitory Properties for Neurite Growth and Fibroblast Spreading" J. Cell Biol., 106:1281-1288 (1988).

Daniels et al., "Membrane targeting of p21-activated kinase 1 (PAK1) induces neurite outgrowth from PC12 cells", The EMBO J., 17(3):754-764 (1988).

Davies et al., "Regeneration of adult axons in white matter tracts of the central nervous system", Nature 390:680-682 (1997).

Kamata et al., "Morphological Effects, Rate of Incorporation, and the Enzymatic Action of Botulinum ADP-Ribosyltransferase, Known as C3 Exoenzyme, of Human Neuroblastoma GOTO Cells,", Microbiol. Immunol., 38(6):421-428 (1994).

Lehmann et al., "Inactivation of Rho Signaling Pathway Promotes CNS Axon Regeneration", J. Neurosci., 19(17):7537-7547 (1999).

Li et al., β- endorphin omission analogs; Dissociation of immunoreactivity from other biological activities Proc., Natl. Acad. Sci. USA, 77(6):3211-3214 (1980).

Liuzzi et al., "Peripheral Nerve Regeneration", Neurosurgery Clinics of North America, 2(1):31-42 91991).

McKerracher et al., "Identification of Myelin-Associated Glycoprotein as a Major Myelin-Derived Inhibitor of Neurite Growth", Neuron, 13:805-811 (1994).

Mattison et al., "Cerebrovascular Diseases: Eighteenth Princeton Conference", Stroke 24(12):I-136-I-140; and Discussion, pp. I-144-I-145.

Nemoto et al., "Clostridium botulinum C3 ADP-ribosyltransferase Gene", J. Biol. Chem., 266(29):19312-19319 (1991).

Saito et al., "Identification of Glu$^{173}$as the critical amino acid residue for the ADP-ribosyltransferase activity of *Clostridium botulinum*C3 exoenzyme", FEBS Letters 371:105-109 (1995).

Olson, "Reparative Strategies in the Brain; Treatment Strategies Based on Trophic Factors and Cell Transfer Techniques", Acta Neurochir. (suppl) 58:3-7 (1993)

Olson et al., "Role of growth factors in degeneration and regeneration in the central nervous system; clinical experiences with NGF in Parkinson's and Alzheimer's diseases", J. Neurol., 241:S12-S15 (1994).

Rubin et al., "Inhibition of PC12 Cell Attachment and Neurite Outgrowth by Detergent Solubilized CNS Myelin Proteins", Eur. J. Neurosci., 7:2524:2529 (1995).

Schwab et al., "Inhibitory influences", Nature, 371:658-659 (1994)..

Tomaselli et al., "N Neuronal Cell Line (PC12) Expresses Two $β_1$-Class Integrins—$α_1β_1$and $α_3β_1$- That Recognize Different Neurite Outgrowth-Promoting Domains in Laminin", Neuron, 5:651-662 (1990).

\* cited by examiner

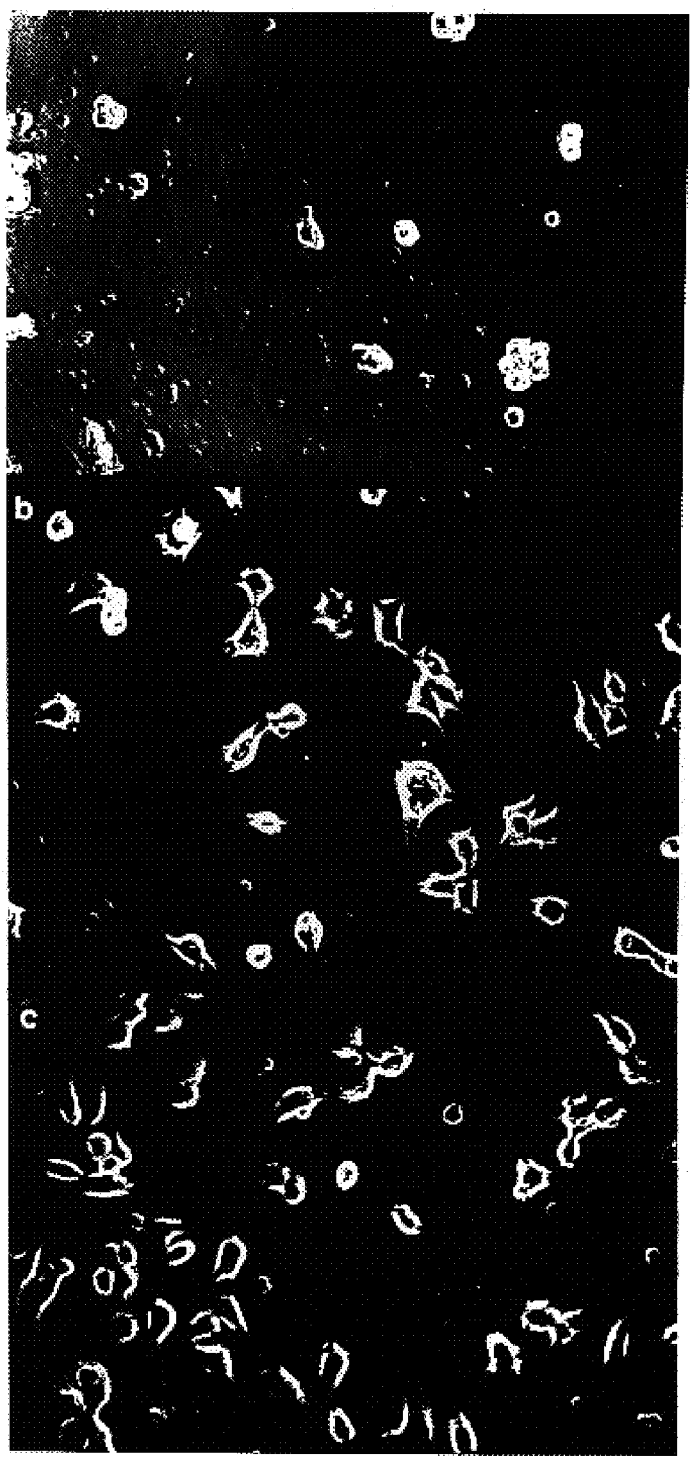
FIG. 1A  MAG
FIG. 1B  MAG + C3
FIG. 1C  PLL

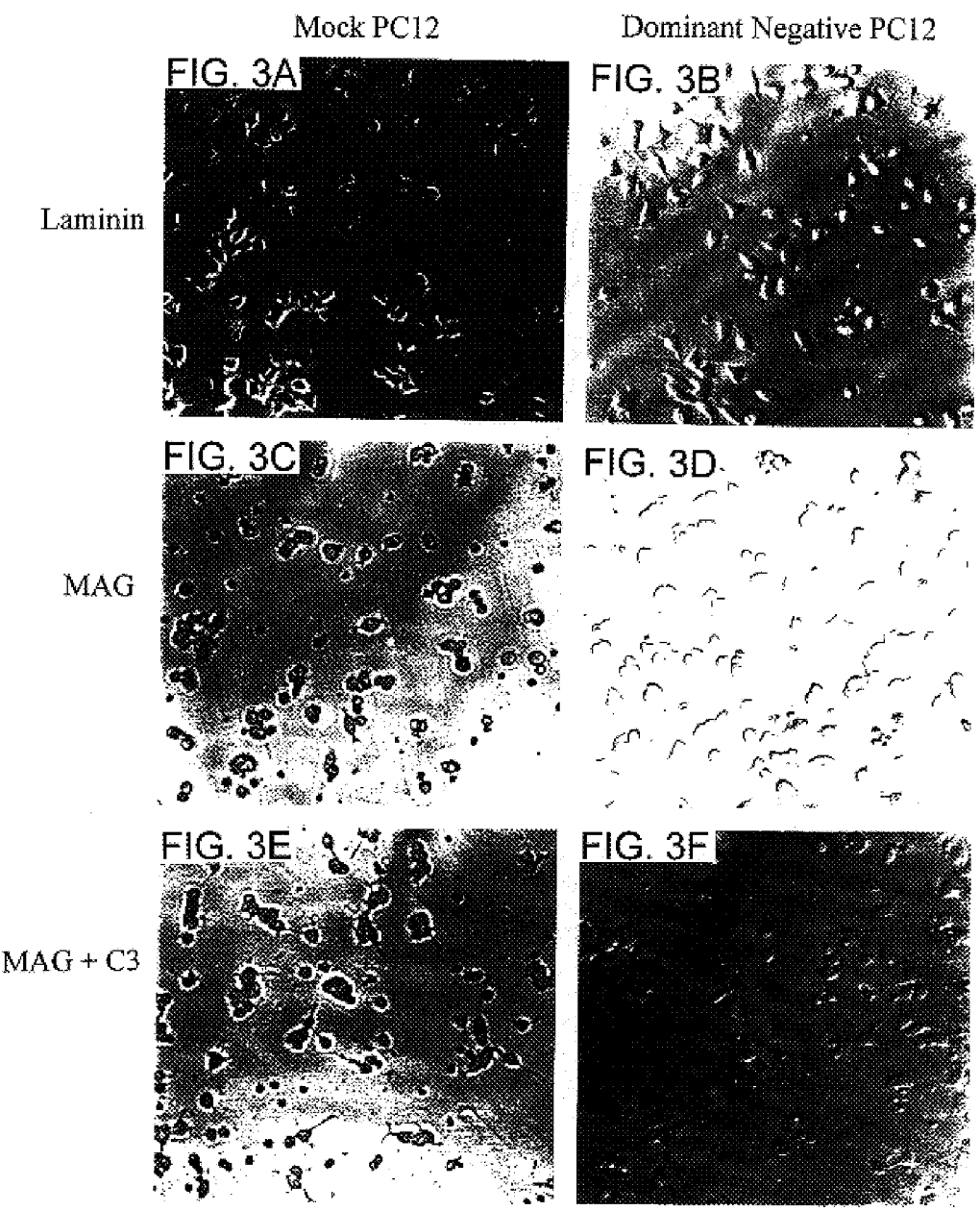

|  | PC12 | RGCs |
|---|---|---|
| C3 | − + | − + |
|  | ▪ ▪  − − | Rho A |
|  | − − − − | CDC42 |

FIG. 6

CRUSH
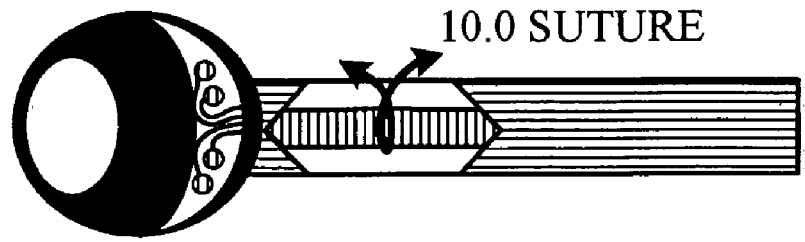
TREATMENT WITH C3 or PBS
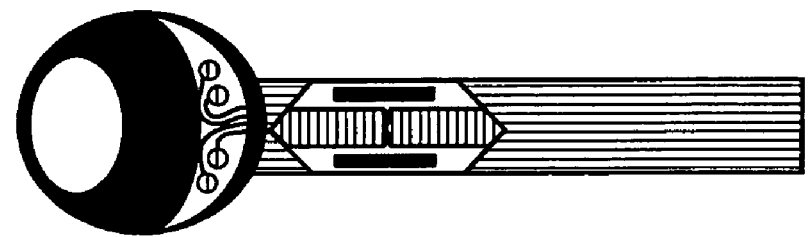
ANTEROGRADE LABELLING
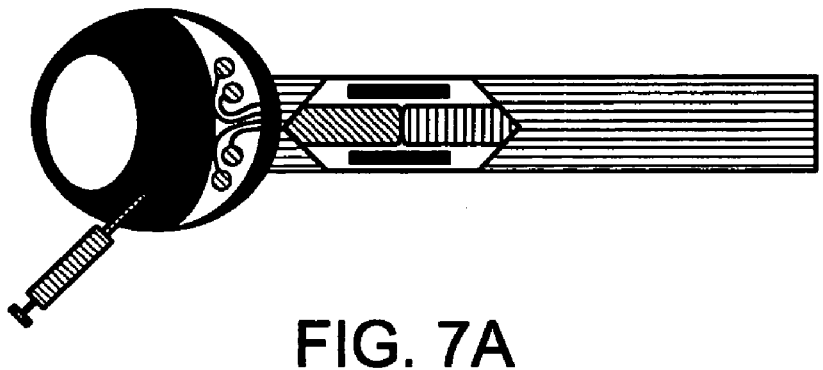
FIG. 7A

(+)-TRANS-4-(1-AMINOETHYL)-1-(4-PYRIDYCARBAMOYL)-CYCLOHEXANE AND METHOD FOR PROMOTING NEURAL GROWTH IN THE CENTRAL NERVOUS SYSTEM AND IN A PATIENT AT A SITE OF NEURONAL LESION

CROSS-REFERENCE TO RELATED APPLICATIONS

This application is a continuation-in-part application of U.S. application Ser. No. 09/184,572 filed on Nov. 2, 1998.

FIELD OF INVENTION

This invention relates to the regulation of growth of neurons in the Central Nervous System.

BACKGROUND

Following trauma in the adult central nervous system (CNS) of mammals, injured neurons do not regenerate their transected axons. An important barrier to regeneration is the axon growth inhibitory activity that is present in CNS myelin and that is also associated with the plasma membrane of oligodendrocytes, the cells that synthesize myelin in the CNS (see Schwab M. E., et al., (1993) *Ann. Rev. Neurosci.* 16, 565–595, for review). The growth inhibitory properties of CNS myelin have been demonstrated in a number of different laboratories by a wide variety of techniques, including plating neurons on myelin substrates or cryostat sections of white matter, and observations of axon contact with mature oligodendrocytes (Schwab, M. E., et al., (1993) *Annu. Rev. Neurosci.* 16 565–595). Therefore, it is well documented that adult neurons cannot extend neurites over CNS myelin in vitro.

It has also been well documented that removing myelin in vivo improves the success of regenerative growth over the native terrain of the CNS. Regeneration occurs after irradiation of newborn rats, a procedure that kills oligodendrocytes and prevents the appearance of myelin proteins (Savio and Schwab, (1990) *Neurobiology* 87, 4130–4133). After such a procedure in rats is combined with a corticospinal tract lesion, some corticospinal axons regrow long distances beyond the lesions. Also, in a chick model of spinal cord repair, the onset of myelination correlates with a loss of its regenerative ability of cut axons (Keirstead, et al., (1992) *Proc. Nat. Acad. Sci.* (USA) 89, 11664–11668). The removal of myelin with anti-galactocerebroside and complement in the embryonic chick spinal cord extends the permissive period for axonal regeneration. These experiments demonstrate a good correlation between myelination and the failure of axons to regenerate in the CNS.

Myelin inhibits axon growth because it contains at least several different growth inhibitory proteins. It has been well documented by us and by others that myelin-associated glycoprotein (MAG) has potent growth inhibitory activity, both in vitro and in vivo (McKerracher, L., et al., (1994) *Neuron* 13, 805–811; Mukhopadhyay, G., et al., (1994) *Neuron* 13, 805–811; Li, M., et al., (1996) *J. Neurosci. Res.* 46, 404–414; Schafer, M., et al., (1996) *Neuron* 16, 1107–1113). A high molecular weight inhibitory activity has been characterized by Schwab and collaborators, and neutralization of this activity with the IN-1 antibody allows some axons to regenerate in white matter (Schwab, M. E., et al., (1993) *Ann. Rev. Neurosci.* 16, 565–595; Bregman, B., et al., (1995) *Nature* 378, 498–501.). We also have evidence that there is an additional growth inhibitory protein in myelin (Xiao, Z., et al., (1997) *Soc. Neurosci. Absts.* 23, 1994). Clearly, there are multiple inhibitory proteins that stop axon regeneration in mammalian CNS myelin.

In addition to the myelin-derived inhibitors there are also other growth inhibitory molecules expressed in the adult mammalian CNS. Tenacin is a growth inhibitory protein that is expressed in some unmyelinated regions of the CNS (Bartsch, U., et al., (1994) *J. Neurosci.* 14, 4756–4768) and after lesion tenascin is expressed by astrocytes that border the lesion site (Ajemain and David (1994) *J. Comp. Neurol.* 340, 233–242). Also growth inhibitory proteins that are proteoglycans are expressed by reactive astrocytes, and these proteins form a barrier to regeneration at the glial scar (McKeon and Silver (1995) *Exp. Neurol.* 136, 32–43).

While axons damaged in the CNS in vivo do not typically regrow, there have been some reports of long distance axon extension in adult white matter. Such growth has been observed following transplantation of grafted neural tissue (Wictorin, K., et al., (1990) *Nature* 347, 556–558; Davies, S. J. A., et al., (1994) *J. Neurosci.* 14, 1596–1612; Isacson, 0. and Deacon, T. W. (1996) *Neuroscience* 75, 827–837), suggesting that embryonic neurons primed for rapid extension of axons may be less susceptible to growth inhibition. Some embryonic neurons are not susceptible to MAG (Mukhopadhyay, G., et al., (1994) *Neuron* 13, 805–811), but most embryonic neurons are inhibited by the other myelin inhibitors (Schwab, M. E., et al, (1993) *Ann. Rev. Neurosci.* 16, 565–595). Therefore, in the cases when axons are able to extend on myelin, signaling through intracellular pathways may play an important role in stimulating, or blocking the inhibition of axon growth. For example, it is known that laminin is able to stimulate rapid neurite growth (Kuhn, T. B., et al., (1995) *Neuron* 14, 275–285), and we have documented that when laminin is present in sufficient concentration, neurites can extend directly on myelin substrates. These findings suggest the possibility that the stimulation of the integrins, the receptors for laminin, is sufficient to allow axon growth on myelin. Similarly, it has been documented that when the adhesion molecule L1 is expressed ectopically on astrocytes, it can partially overcome their non-permissive substrate properties (Mohajeri, M. H., et al., (1996) *Eur. J. Neurosci.* 8, 1085–1097). Therefore, neurons can, under appropriate conditions, grow axons on inhibitory substrates, suggesting that the balance of positive to negative growth cues is a critical determinant for the success or failure of axon regrowth after injury.

Growth inhibitory proteins typically cause growth cone collapse, a process that causes dramatic rearrangements to the growth cone cytoskeleton (Bandtlow, C. E., et al., (1993) *Science* 259, 80–83; Fan, J., et al., (1993) *J. Cell Biol.* 121 867–878; Li, M., et al., (1996) *J. Neurosci. Res.* 46, 404–414). One family of proteins that has been implicated in receptor-medicated signaling to the cytoskeleton is the small GTPases of the Rho family (Hall, A. (1996) *Ann. Rev. Cell Biol.* 10, 31–54). In non-neuronal cells it has been clearly documented that mutations in Rho family members that include Rho, Rac and cdc42, affect adhesion, actin polymerization, and the formation of lamellipodia and filopodia, which are all processes important to motility (Nobes, C. D. and Hall, A. R. (1995) *Cell* 81, 53–62). There is now good evidence that members of the Rho family regulate axon outgrowth in development. Mutations in Rho-related family members block the extension of axons in Drosophila (Luo, L., et al., (1994) *Genes Dev.* 8, 1787–1802) and disrupt axonal pathfinding in *C. elegans* (Zipkin, I. L., et al., (1997) *Cell* 90, 883–894). More recently it has been shown that the guidance molecule collapsin acts through a Rac-dependent mechanism (Jin, Z. and Strittmatter, S. M. (1997) *J. Neurosci.* 17, 6256–6263). In transgenic mice that express constitutively active Rac in Purkinje cells, there are alterations in the development of axon terminals and dendritic arborizations (Luo, L., et al., (1996) *Nature* 379, 837–840). Consistent with the observations in vivo, it was found that dominant negative Rac expressed in PC12 cells disrupts neurite outgrowth in response to NGF (Hutchens, J. A., et al., (1997) *Molec. Biol. Cell* 8, 481–500). Also, treatment of PC 12 cells with lysophosphatidic acid, a mitogenic phospholipid, causes neurite retraction that is mediated by Rho (Tigyi, G., et al., (1996) *J. Neurochem.* 66, 537–548). Therefore, different members of the Rho family can exert distinct effects on neurite growth, and in PC 12 cells the activation of Rho is correlated with growth cone collapse. In non-neuronal cells, Rho participates in integrin-dependent signaling (Laudanna, C., et al., (1996) *Science* 271, 981–983; Udagawa, T. and McIntyre, B. W. (1996) *J. Biol. Chem.* 271, 12542–12548). The possibility that Rho might play a role within the myelin-derived growth inhibitory system has been studied (Jin, Z. and Strittmatter, S.M. (1997) *J. Neurosci.* 17, 6256–6263). It was concluded, however, that the inhibitory effects of myelin are not mediated by Rho family members.

A need remains for a means of inactivating the multiple inhibitory proteins present in myelin that prevent axonal regrowth after injury in the CNS.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates to antagonists and inhibitors to members of the Rho family of proteins and diagnostic, therapeutic, and research uses for each of these aspects. In particular, members of the Rho family of proteins serve as a therapeutic target to foster regrowth of injured or degenerating axons in the CNS.

In accordance with the present invention, a preferred embodiment relates to antagonists and inhibitors of members of the Rho family of proteins and their use as a means of blocking a common signaling pathway used by the diverse growth inhibitory molecules. The antagonists and inhibitors may be mutated forms of Rho and biologically active (Rho family-inhibitory) fragments, peptides, C3 and biologically active (Rho family-inhibitory) fragments, or small molecules such as Y-27632.

In yet a further aspect of the present invention, Rho family member proteins can be used to design small molecules that antagonize and inhibit Rho family proteins, to block inhibition of neurite outgrowth. In another aspect of the present invention Rho family members can be used to design antagonist agents that suppress the myelin growth inhibitory system. These antagonist agents can be used to promote axon regrowth and recovery from trauma or neurodegenerative disease.

In a further aspect of the present invention, inhibitors of the Rho family of proteins can be used to block inhibition of neurite outgrowth and to suppress the myelin growth inhibitory system. Such inhibitors could block exchange of the GTP/GDP cycle of Rho activation/inactivation.

A further embodiment involves a method of suppressing the inhibition of neuron growth, comprising the steps of delivering to the nerve growth environment, antibodies directed against Rho family members in an amount effective to reverse said inhibition.

In accordance with another aspect of the present invention, there is provided an assay method useful to identify Rho family member antagonist agents that suppress inhibition of neuron growth, comprising the steps of:

a) culturing neurons on a growth permissive substrate that incorporates a growth-inhibiting amount of a Rho family member; and b) exposing the cultured neurons of step a) to a candidate Rho family member antagonist agent in an amount and for a period sufficient prospectively to permit growth of the neurons;

thereby identifying as Rho family antagonists the candidates of step b) which elicit neurite outgrowth from the cultured neurons of step a).

In accordance with another aspect of present invention, there is provided a method to suppress the inhibition of neuron, comprising the steps of delivering, to the nerve growth environment, a Rho family antagonist in an amount effective to reverse said inhibition.

In another embodiment, kinases activated by Rho, such as Rho-associated kinase, are antagonist candidates. Thus, compounds such as Y-27632 (U.S. Pat. No. 4,997,834), that block Rho-associated kinase activity, thereby inactivating the Rho signaling pathway, are also embodiments of this invention. Thus, the use of other compounds within this family of compounds as described in U.S. Pat. No. 4,997,834 that inhibit Rho kinase are also considered within the scope of this invention.

In another embodiment, the nucleic acids encoding Rho family members can be used in antisense techniques and therapies.

In yet another embodiment, a kit is provided comprising components necessary to conduct the assay method useful to screen Rho family antagonist agents.

Various other objects and advantages of the present invention will become apparent from the detailed description of the invention.

BRIEF DESCRIPTION OF DRAWINGS

FIG. 1 shows results of treatment with C3 to stimulate neurite outgrowth on inhibitory MAG substrates. FIG. 1A shows PC12 cells plated on MAG remained rounded and did not extend neurites. FIG. 1B shows cells plated on MAG in the presence of C3 grew neurites. FIG. 1C shows PC12 cells plated on polylysine (PLL) substrates as a positive control.

FIG. 3 presents the results of studies in which PC12 cells transfected with dominant negative Rho extend short neurites on MAG substrates. Mock-transfected PC12 cells (FIGS. 3A, C, and E) or cells transfected with dominant-negative Rho (FIGS. 3B, D, and F) were plated on laminin (FIGS. 3A and B) or MAG (FIGS. 3C–F). MAG inhibits neurite outgrowth (FIG. 3C), but dominant negative Rho cells spread on MAG and some cells extend short neurites (FIG. 3D). Treatment with C3 further stimulates neurite outgrowth on MAG from both lines of cells (FIGS. 3E and F).

FIG. 6 demonstrates ADP-ribosylation of Rho by C3 detected in cultured cells. PC12 cells or retinal neurons were cultured in the presence (+) or absence of C3 (−) for two days. The cells were lysed, and 10 µg of protein from each sample was separated on a 11% acrylamide gel. The proteins were transferred to nitrocellulose, probed with mouse anti-RhoA antibody and anti-mouse-HRP antibody, and revealed by a chemiluminescent reaction (top panel). The membranes were then reprobed with rabbit anti-Cdc42 and anti-rabbit alkaline phosphatase and revealed with NTB/BCIP color reaction (bottom panel). Treatment of cells with C3 results in an ADP-ribosylation-induced decrease in the mobility of RhoA. The mobility of Cdc42 does not change with C3 treatment.

FIG. 7 illustrates methods used to study the effect of C3 on injured optic nerve. FIG. 7A shows the optic nerve was removed from the sheath prior to crushing with 10.0 sutures (top panel) and C3 was applied in Gelfoam and Elvax tubes (rectangular bars in middle and bottom panels) immediately following optic nerve crush (middle panel). The retinal ganglion cell axons were detected by anterograde labeling with cholera toxin and immunodetection of the cholera toxin in longitudinal sections of the optic nerve (bottom panel). (FIG. 7C) Longitudinal 15 µm section of a buffer-treated control optic nerve showing the failure of RGC axons to cross the injured region; (FIGS. 7D and E) Longitudinal 15 µm sections of two different optic nerves treated with C3 showing anterogradely-labeled axons extending past the crush (arrows). The site of crush is indicated with arrowheads; (FIG. 7F) Higher magnification view in FIG. 2E showing the twisted growth of regenerating axons. Bar, 100 µm (FIGS. 7C–E) and 50 µm in FIG. 7F.

DETAILED DESCRIPTION OF THE INVENTION

Figure 2A:
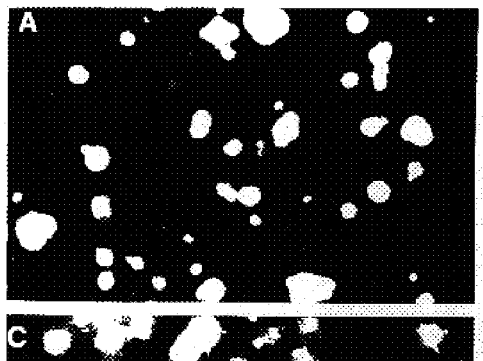
FIG. 2 shows the role of integrins in overriding growth inhibition by myelin. The anti-α1 integrin function blocking antibody, 3A3, was used to determine if integrin function is necessary for laminin to override growth inhibition by myelin or MAG For experiments on myelin substrates (FIGS. 2A–D), cells were fluorescently labeled with DiI, and plated on myelin (FIG. 2A), polylysine (FIG. 2B), or myelin ±1 µg laminin (FIGS. 2C and D). Control IgG was added to samples shown in FIGS. 2A–C, the 3A3 antibody to the sample shown in FIG. 2D. Neurites do not extend on myelin but grow on laminin or mixed lamininlmyelin substrates. When 3A3 is added, laminin no longer overrides growth inhibition by myelin.
FIGS. 2E–H show by phase contrast cells plated on recombinant MAG (FIG. 2E), laminin (FIG. 2F), or recombinant MAG plus laminin (FIGS. 2G and H), with control antibody (FIGS. 2E–G) or with 3A3 (FIG. 2H). Integrin function is needed to override growth inhibition by MAG.
Figure 2B:
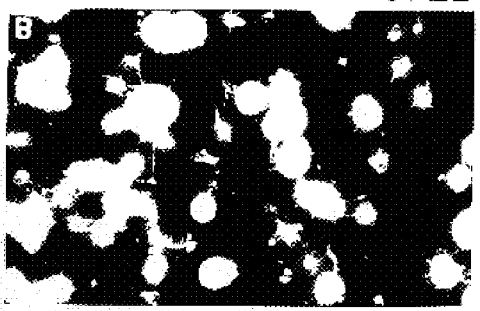
Figure 2C:
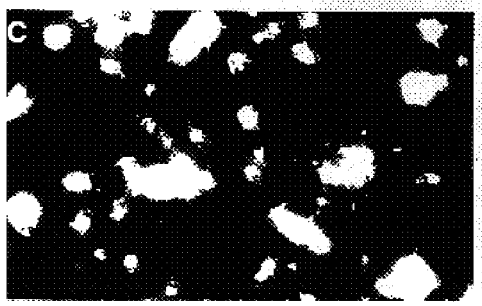
Figure 2D:
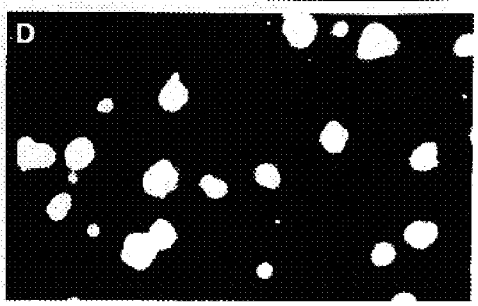
Figure 2E:
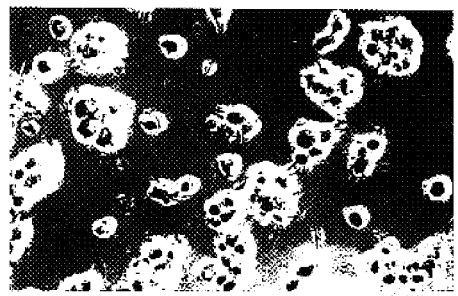
Figure 2F:
Figure 2G:
Figure 2H:
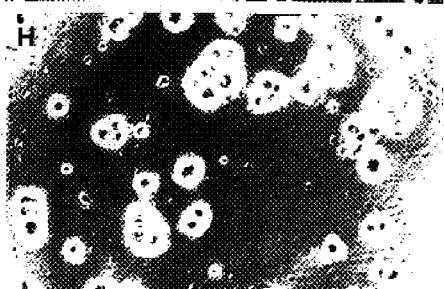

This invention arises from the discovery that Rho family members are key molecules in regulating inhibition by myelin proteins, and by MAG. Thus, this invention provides the advantage of identifying an intracellular target, Rho family members, for all of the multiple inhibitory proteins that must be inactivated to allow for growth on myelin. The method of this invention provides for inactivation of Rho family members, thereby stimulating neurite growth on growth inhibitory substrates. Therefore, antagonists that inactivate Rho family members in vivo should allow axon regeneration in the injured or diseased CNS.

This invention provides for the use of Rho, or proteins related to Rho as therapeutic targets for agents designed to block growth inhibition by myelin or myelin proteins. One embodiment pertains to the use of Rho antagonists that foster axon regeneration in the central nervous system. The therapeutic agent or antagonist can be small molecules, proteins or peptides, or any agent that binds to Rho or its family members to inactivate this pathway.

Another embodiment pertains to the use of the Rho regulatory pathway as a target for Rho antagonists. This pathway involves the GDP/GTP exchange proteins (GEPs). Rho has two interconvertible forms, GDP-bound inactive, and GTP-bound active forms. The GEPs promote the exchange of nucleotides and thereby constitute targets for regulating the activity of Rho. In another embodiment GDP dissociation inhibitors (GDPs) inhibit the dissociation of GDP from Rho, and thereby prevent the binding of GTP necessary for the activation of Rho. Therefore, GDIs are targets for agents that regulate Rho activity. The GTP-bound active Rho can be converted to the GDP-found inactive form by a GTPase reaction that is facilitated by its specific GTPase activating protein (GAP). Thus, another embodiment pertains to the use of GAPs as targets for the regulation of Rho activity. Another embodiment pertains to the fact that Rho is found in the cytoplasm complexed with a GTPase inhibiting protein (GDI). To become active, Rho binds GTP and is translocated to the membrane. Thus, agents that affect Rho binding to the plasma membrane are also considered within the scope of this invention. Yet another embodiment pertains to the observation that a bacterial mon-ADP ribosyltransferase, C3 transferase, ribosylates Rho to inactivate the protein. Thus this embodiment pertains to the use of C3 transferase to inactivate Rho and stimulate axon growth. Likewise, other bacterial toxins, such as toxins A and B, with related Rho-inhibitory activity are considered to be within the scope of this invention. Moreover, various mutations of the Rho protein can create dominant negative Rho, which can interfere with the biological activity of endogenous Rho in neurons. Thus, yet a further embodiment of this invention pertains to the use of dominant negative forms of Rho, used to inactivate Rho, to foster axon growth.

"Antagonist" refers to a pharmaceutical agent which in accordance with the present invention which inhibits at least on biological activity normally associated with Rho family members, that is blocking or suppressing the inhibition of neuron growth. Antagonists which may be used in accordance with the present invention include without limitation, one or more Rho family members fragment, a derivative of Rho family members or of a Rho family members fragment, an analog of Rho family members or of a Rho family members fragment or of said derivative, and a pharmaceutical agent, and is further characterized by the property of suppressing Rho family members-mediated inhibition of neurite outgrowth. Preferred antagonists include: mutated forms of Rho, such as Rho wherein the effector Domain, A-37, has been mutated to prevent GTP exchange; the ADP-ribosyl transferase C3 and biologically effective fragments that antagonize Rho family members in one of the assays of this invention; and compounds such as Y-27632 that antagonise Rho-associated kinase (Somiyo, 1997, Nature, 389:908–910; Uehata, et al., 1997, Nature 389: 990–994; U.S. Pat. No. 4,997,834).

The antagonist of Rho family members in accordance with the present invention is not limited to Rho family members or its derivatives, but also includes the therapeutic application of all agents, referred herein as pharmaceutical agents, which alter the biological activity of the Rho family members protein such that inhibition of neurons or their axon is suppressed.

The term "effective amount" or "growth-promoting amount" refers to the amount of pharmaceutical agent required to produce a desired antagonist effect of the Rho family members biological activity. The precise effective amount will vary with the nature of pharmaceutical agent used and may be determined by one or ordinary skill in the art with only routine experimentation.

As used herein, the Rho family of proteins comprises, but is not limited to rho, rac, cdc42 and their isotypes, such as RhoA, RhoB, RhoC, as well as Rho-associated kinases that are expressed in neural tissue. Other members of the Rho family that are determined and whose inhibition of activity allows for neurite outgrowth are contemplated to be part of this invention. (See, for example, Katoh, H., et al., J. Biol. Chem., 273:2489–2492, 1998; van Leeuwen, F., et al., J. Cell Biol., 139:797–807, 1997; Matsui et al., EMBO J. 15:2208–2216, 1996; Amano et al., Science, 275:1308; Ishizaki, T. et al., (1997) FEBS Lett., 404:118–124).

As used herein, the terms "Rho family member biological activity" refers to cellular events triggered by, being of either biochemical or biophysical nature. The following list is provided, without limitation, which discloses some of the known activities associated with contact-mediated growth inhibition of neurite outgrowth, adhesion to neuronal cells, and promotion of neurite out growth from new born dorsal root ganglion neurons.

As used herein, the term "biologically active", or reference to the biological activity of Rho family members, or polypeptide fragment thereof, refers to a polypeptide that is able to produce one of the functional characteristics exhibited by Rho family members or its receptors described herein. In one embodiment, biologically active proteins are those that demonstrate inhibitory growth activities central nervous system neurons. Such activity may be assayed by any method known to those of skill in the art.

The term C3 refers to C3 ADP-ribosyltransferase, a specific Rho inactivator. A preferred representative example is C3 ADP-ribosyltransferase, a 23 KDa exoenzyme secreted from certain strains of types C and D from Clostridium botulinum, which specifically ADP-ribosylates the rho family of these GTP-binding proteins. This ADP-ribosylation occurs at a specific asparagine residue in their putative effector domain, and presumably interferes with their interaction with a putative effector molecule downstream in signal transduction. Numerous references describing these compounds can be found in *Methods in Enzymology*, Vol 256, Part B, Eds.; W. E. Balch, C. H. Der, and A. Hall; Academic Press, 1995, for e.g. Pgs. 196–206, 207 et seq, 184–189 and 174 et seq.

Based on the present evidence that Rho family members can affect growth inhibitory protein signals in myelin, the means exist to identify agents and therapies that suppress myelinmediated inhibition of nerve growth. Further, one can exploit the growth inhibiting properties of Rho family members, or Rho family members antagonists, to suppress undesired nerve growth. Without the critical finding that a Rho family member has growth inhibitory properties, these strategies would not be developed.

Rho Family Member Antagonists and Assay Methods to Identify Rho Family Members Antagonists In one embodiment, Rho family member antagonists will be inhibitors of GTPase activity. The GTP/GDP cycle of Rho family members activation/inactivation is regulated by a number of exchange factors. Compounds that block exchange, thereby inactivating Rho family members are preferred embodiments of this invention.

In another embodiment suitable Rho family member antagonist candidates are developed comprising fragments, analogs and derivatives of Rho family members. Sequences for Rho family members are known, such as those described: Chardin, P., et al., (1988) Nucleic Acids Research, 16:2717; Yeramian, et al., (1987) Nucleic Acids Research, 15: 1869). Such candidates may interfere with Rho family members-mediated growth inhibition as competitive but non-functional mimics of endogenous Rho family members. From the amino acid sequence of Rho family members and from the cloned DNA coding for it, it will be appreciated that Rho family members fragments can be produced either by peptide synthesis or by recombinant DNA expression of either a truncated domain of Rho family members, or of intact Rho family members could be prepared using standard recombinant procedures, that can then be digested enzymatically in either a random or a site-selective manner. Analogs of Rho family members or Rho family members fragments can be generated also by recombinant DNA techniques or by peptide synthesis, and will incorporate one or more, e.g. 1–5, L- or D-amino acid substitutions. Derivatives of Rho family members, Rho family members fragments and Rho family members analogs can be generated by chemical reaction of the parent substance to incorporate the desired derivatizing group, such as N-terminal, C-terminal and intra-residue modifying groups that have the effect of masking or stabilizing the substance or target amino acids within it.

In specific embodiments of the invention, candidate Rho family member antagonists include those that are derived from a determination of the functionally active region(s) of Rho family member. The antibodies mentioned above and any others to be prepared against epitopes in Rho family members, when found to be function-blocking in in vitro assays, can be used to map the active regions of the polypeptide as has been reported for other proteins (for example, see Fahrig, et al., (1993) *Europ. J Neurosci.*, 5 1118–1126; Tropak, et al., (1994) *J. Neurochem.*, 62, 854–862). Thus, it can be determined which regions of Rho family members GTPases recognized by substrate molecules that are involved in inhibition of neurite outgrowth. When those are known, synthetic peptides can be prepared to be assayed as candidate antagonists of the Rho family members effect. Derivatives of these can be prepared, including those with selected amino acid substitutions to provide desirable properties to enhance their effectiveness as antagonists of the Rho family members candidate functional regions of Rho family members can also be determined by the preparation of altered forms of the Rho family members domains using recombinant DNA technologies to produce deletion or insertion mutants that can be expressed in various cell types as chimeric proteins. All of the above forms of Rho family members, and forms that may be generated by technologies not limited to the above, can be tested for the presence of functional regions that inhibit or suppress neurite outgrowth, and can be used to design and prepare peptides to serve as antagonists.

In accordance with an aspect of the invention, the Rho family member antagonist is formulated as a pharmaceutical composition which contains the Rho family member antagonist in an amount effective to suppress Rho family member-mediated inhibition of nerve growth, in combination with a suitable pharmaceutical carrier. Such compositions are useful, in accordance with another aspect of the invention, to suppress Rho family member-inhibited nerve growth in patients diagnosed with a variety of neurological disorders, conditions and ailments of the PNS and the CNS where treatment to increase neurite extension, growth, or regeneration is desired, e.g., in patients with nervous system damage. Patients suffering from traumatic disorders (including but not limited to spinal cord injuries, spinal cord injuries, spinal cord lesions, surgical nerve lesions or other CNS pathway lesions) damage secondary to infarction, infection, exposure to toxic agents, malignancy, paraneoplastic syndromes, or patients with various types of degenerative disorders of the central nervous system can be treated with such Rho family members antagonists. Examples of such disorders include but are not limited to Strokes, Alzheimer's disease, Down's syndrome, Creutzfeldt-Jacob disease, kuru, Gerstman-Straussler syndrome, scrapie, transmissible mink encephalopathy, Huntington's disease, Riley-Day familial dysautonomia, multiple system atrophy, amylotrophic lateral sclerosis or Lou Gehrig's disease, progressive supranuclear palsy, Parkinson's disease and the like. The Rho family members antagonists may be used to promote the regeneration of CNS pathways, fiber systems and tracts. Administration of antibodies directed to an epitope of Rho family member, or the binding portion thereof, or cells secreting such antibodies can also be used to inhibit Rho family member function in patients. In a particular embodiment of the invention, the Rho family members antagonist is used to promote the regeneration of nerve fibers over long distances following spinal cord damage.

In another embodiment, the invention provides an assay method adapted to identify a Rho family member antagonists, that is agents that block or suppress the growth-inhibiting action of Rho family members. In its most convenient form, the assay is a tissue culture assay that measures neurite out-growth as a convenient end-point, and accordingly uses nerve cells that extend neurites when grown on a permissive substrate. Nerve cells suitable in this regard include neuroblastoma cells of the NG108 lineage, such as NG108–15, as well as other neuronal cell lines such as PC12 cells (American Type Culture Collection, 12301 Parklawn Drive, Rockville, Md. 20852 USA, ATCC Accession No. CRL 1721), human neuroblastoma cells, and primary cultures of CNS or PNS neurons taken from embryonic, postnatal or adult animals. The nerve cells, for instance about $10^3$ cells-microwell or equivalent, are cultured on a growth permissive substrate, such as polylysine or laminin, that is over-layed with a growth-inhibiting amount of Rho family members. The Rho family members incorporated in the culture are suitable myelin-extracted Rho family members, although forms of Rho family members other than endogenous forms can be used provided they exhibit the Rho family members property of inhibiting neuron growth when added to a substrate that is otherwise growth permissive.

In this assay, candidate Rho family member antagonists, i.e., compounds that block the growth-inhibiting effect of Rho family members, are added to the Rho family member containing tissue culture preferably in amount sufficient to neutralize the Rho family member growth-inhibiting activity, that is between 1.5 and 15 μg of Rho family members antagonist per well containing a density of 1000 NG108-15 cells/well cultured for 24 hr. in Dulbecco's minimal essential medium. After culturing for a period sufficient for neurite outgrowth, e.g. 3–7 days, the culture is evaluated for neurite outgrowth, and antagonists are thereby revealed as those candidates, which elicit neurite outgrowth. Desirably, candidates selected as Rho family members antagonists are those which elicit neurite outgrowth to a statistically significant extent, e.g., in at least 50%, more desirably at least 60%, e.g. 70%, per 1,000 cultured neurons.

Other assay tests that could be used include without limitation the following: 1) The growth cone collapse assay that is used to assess growth inhibitory activity of collapsin (Raper, J. A., and Kapfhammer, J. P., (1990) *Neuron*, 2, 21–29; Luo, L., et al., (1993) *Cell* 75, 217–227) and of various other inhibitory molecules (Igarashi, M., et al., (1993) *Science* 259, 77–79) whereby the test substance is added to the culture medium and a loss of elaborate growth cone morphology is scored. 2) The use of patterned substrates to assess substrate preference (Walter, J. et al., (1987) *Development* 101, 909–913; Stahl, et al, (1990) *Neuron* 5, 735–743) or avoidance of test substrates (Ethell, D. W., et al., (1993) *Dev. Brian Res.* 72, 1–8). 3) The expression of recombinant proteins on a heterologous cell surface, and the transfected cells are used in co-culture experiments. The ability of the neurons to extend neurites on the transfected cells is assessed (Mukhopadhyay et al., (1994) *Neuron* 13, 757,767). 4) The use of sections of tissue such as sections of CNS white matter, to assess molecules that may modulate growth inhibition (Carbonefto, S., et al., (1987) *J. Neuroscience* 7, 610–620; Salvo, T. and Schwab, M. E., (1989) *J. Neurosci.*, 9:1126–1133). 5) Neurite retraction assays whereby test substrates are applied to differentiated neural cells for their ability to induce or inhibit the retraction of previously extended neurites (Jalnink, et al., (1994) *J. Cell Bio.* 126, 801–810; Sudan, H. S., et al., (1992) Neuron 8, 363–375; Smalheiser, N., (1993) *J. Neurochem.* 61, 340–342). 6) The repulsion of cell-cell interactions by cell aggregation assays (Kelm, S., et al., (1994) *Current Biology* 4, 965–972; Brady-Kainay, S., et al., (1993) *J. Cell Biol.* 4, 961–972). 7) The use of nitrocellulose to prepare substrates for growth assays to assess the ability of neural cells to extend neurites on the test substrate (Laganeur, C. and Lemmon, V., (1987) *PNAS* 84, 7753–7757; Dou, C-L and Levine, J. M., (1994) *J. Neuroscience* 14, 7616–7628).

Diagnostic, Therapeutic and Research Uses for Rho Family Member Antagonists

Rho family member antagonists have uses in diagnostics. Such molecules can be used in assays to detect, prognose, diagnose, or monitor various conditions, diseases, and disorders affecting neurite growth extension, invasiveness, and regeneration. Alternatively, the Rho family member antagonists may be used to monitor therapies for diseases and conditions which ultimately result in nerve damage; such diseases and conditions include but are not limited to CNS trauma, (e.g. spinal cord injuries), infarction, infection, malignancy, exposure to toxic agents, nutritional deficiency, paraneoplastic syndromes, and degenerative nerve diseases (including but no limited to Alzheimer's disease, Parkinson's disease, Huntington's Chorea, amyotrophic lateral sclerosis, progressive supra-nuclear palsy, and other dementias). In a specific embodiment, such molecules may be used to detect an increase in neurite outgrowth as an indicator of CNS fiber regeneration. For example, in specific embodiments, altered levels of Rho family members activity in a patient sample containing CNS myelin can be diagnostic marker for the presence of a malignancy, including but not limited to glioblastoma, neuroblastoma, and melanoma, or a condition involving nerve growth, invasiveness, or regeneration in a patient.

Useful for nerve growth suppression are pharmaceutical compositions that contain, in an amount effective to suppress nerve growth, Rho family member antagonist in combination with an acceptable carrier. Candidate Rho family members antagonists include fragments of Rho family members that incorporate the ectodomain, including the ectodomain per se and other N- and/or C-terminally truncated fragments of Rho family members or the ectodomain, as well as analogs thereof in which amino acids, e.g. from 1 to 10 residues, are substituted, particularly conservatively, and derivatives of Rho family members or Rho family members fragments in which the N- and/or C-terminal residues are derivatized by chemical stabilizing groups.

In a preferred embodiment, mutated forms of Rho family members are used as antagonists. One key example is Rho with a mutated effector domain, A-37, which prevents GTP exchange. Various other mutations of the Rho protein that create dominate negative Rho which can interfere with the biological activity of endogenous Rho in neurons are considered as antagonists within the scope of this invention to inactivate Rho, thereby fostering growth of neurons. In another preferred embodiment GDP dissociation inhibitors (GDIs), which inhibit the dissociation of GDP from Rho, and thereby prevent the binding of GTP necessary for the activation of Rho are used as antagonists.

In yet another preferred embodiment, GTPase activating protein (GAP) which facilitates the conversion of the GTP-bound active Rho to the GDP-bound inactive form forms the target for regulation of Rho activity. Thus, compounds that activate GAP, thereby facilitating the conversion of active Rho into inactive Rho.

In still another preferred embodiment, compounds that affect Rho binding to the plasma membrane, thereby decreasing the activity of Rho are also considered Rho antagonists of this invention. In this case, the target design is based on the knowledge that Rho is found in the cytoplasm complexed with GTPase inhibiting protein (GDI). To become active, Rho binds GTP and is translocated to the membrane. Thus, agents that induce Rho binding to the plasma membrane would decrease Rho activity.

In specific embodiments of the invention, candidate Rho family members antagonists include specific regions of the Rho family members molecule, and analogs or derivatives of these. These can be identified by using the same technologies described above for identification of Rho family members regions that serve as inhibitors of neurite outgrowth.

The Rho family members related derivatives, analogs, and fragments of the invention can be produced by various methods known in the art. The manipulations, which result in their production can occur at the gene or protein level. For example, Rho family members-encoding DNA can be modified by any of numerous strategies known in the art (Maniatis et al., Molecular Cloning, A Laboratory Manual, Cold Spring Harbor Laboratory, Cold Spring Harbor, N.Y., 1982), such as by cleavage at appropriate sites with restriction endonuclease(s), subjected to enzymatic modifications if desired, isolated, and ligated in vitro.

Additionally, the Rho family members-encoding gene can be mutated in-vitro or in-vivo for instance in the manner applied for production of the ectodomain, to create and/or destroy translation, initiation, and/or termination sequences, or to create variations in coding regions and/or form new restriction endonuclease sites or destroy preexisting ones, to facilitate further in-vitro modification. Any technique for mutagenesis known in the art can be used, including but not limited to, in-vitro site directed mutagenesis (Hutchinson, et al., (1978) *J. Biol. Chem.* 253, 6551), use of TAB™ linkers (Pharmacia), etc.

For delivery of Rho family members antagonists, various known delivery systems can be used, such as encapsulation in liposomes or semipermeable membranes, expression in suitably transformed or transfection glial cells, oligodendroglial cells, fibroblasts, etc. according to the procedure known to those skilled in the are (Lindvall, et al., (1994) *Curr. Opinion Neurobiol.* 4, 752–757). Linkage to ligands such as antibodies can be used to target delivery to myelin and to other therapeutically relevant sites in-vivo. Methods of introduction include, but are not limited to, intradermal, intramuscular, intraperitoneal, intravenous, subcutaneous, oral, and intranasal routes, and transfusion into ventricles or a site of operation (e.g. for spinal cord lesions) or tumor removal. Likewise, cells secreting Rho family members antagonist activity, for example, and not by way of limitation, hybridoma cells encapsulated in a suitable biological membrane may be implanted in a patient so as to provide a continuous source of Rho family members inhibitor.

Therapeutic Uses of Rho family Antagonists

In an embodiment, antagonists, derivatives, analogs, inhibitors of Rho family members can be used in regimens where an increase in neurite extension, growth, or regeneration is desired, e.g., in patients with nervous system damage. Patients suffering from traumatic disorders (including but not limited to spinal cord injuries, spinal cord lesions, or other CNS pathway lesions), surgical nerve lesions, damage secondary to infarction, infection, exposure to toxic agents, malignancy, paraneoplastic syndromes, or patients with various types of degenerative disorders of the central nervous system can be treated with such inhibitory protein antagonists. Examples of such disorders include but are not limited to Alzheimer's Disease, Parkinson's Disease, Huntington's Chorea, amyotrophic lateral sclerosis, progressive supranuclear palsy and other dementias. Such antagonists may be used to promote the regeneration of CNS pathways, fiber systems and tracts. Administration of antibodies directed to an epitope of, (or the binding portion thereof, or cells secreting such as antibodies) can also be used to inhibit Rho family members protein function in patients. In a particular embodiment of the invention, antibodies directed to Rho family members may be used to promote the regeneration of nerve fibers over long distances following spinal cord damage.

Various delivery systems are known and can be used for delivery of antagonists or inhibitors of Rho family members and related molecules, e.g., encapsulation in liposomes or semipermeable membranes, expression by bacteria, etc. Linkage to ligands such as antibodies can be used to target myelin associated protein-related molecules to therapeutically desirable sites in vivo. Methods of introduction include but are not limited to intradermal, intramuscular, intraperitoneal, intravenous, subcutaneous, oral, and intranasal routes, and infusion into ventricles or a site of operation (e.g. for spinal cord lesions) or tumor removal.

In addition, any method which results in decreased synthesis of Rho family members may be used to diminish their biological function. For example, and not by way of limitation, agents toxic to the cells which synthesize Rho family members and/or its receptors (e.g. oligodendrocytes) may be used to decrease the concentration of inhibitory proteins to promote regeneration of neurons.

EXAMPLES

Example 1

This example demonstrates in vitro evidence that Rho family members are responsible for regulating the neuronal response to MAG. In particular, this demonstrates that the small GTPase Rho regulates the response to MAG. PC12 cells were planted on polysine (PLL), laminin, or MAG substrates and exposed to NGF to stimulate neurite growth. PC 12 cells differentiated neurites on PLL and laminin substrates, but on MAG substrates the cells remained rounded and did not grow neurites.

The addition of the ADP-ribosyl transferase C3 from *Clostidium botulinum*, that efficiently inactivates Rho family members without affecting Rac and cdc42 (Udagawa, T. and McIntyre, B. W. (1996) *J. Biol. Chem*. 271, 12542–12548), allowed the cells to extend neurites on MAG substrates. In addition this example demonstrates neurite growth from PC 12 cells transfected with a dominant negative N19RhoA construct. On laminin and PLL substrates the N19 RhoA PC 12 cells grew neurites that were longer than the mock-transfected controls. Moreover, N19 RhoA PC12 cells were able to extend neurites when plated on MAG substrates. Therefore, the inactivation of Rho stimulates neurite outgrowth and allows neurite extension on MAG substrates. These results implicate Rho in signaling growth inhibition by MAG.

Cell Culture

We obtained PC 12 cells from three different sources: from Dr. Phil Barker (Montreal Neurological Institute); from the ATCC (obtained from W. Mushinsky, McGill), and from Gabor Tigyi, (University of Tennessee) and we found that all lines of cells were inhibited by both myelin and MAG. PC12 cells were grown in Dulbecco's modified eagle's medium (DMEM) with 10% horse serum and 5% fetal bovine serum. PC 12 cells stably transfected with constitutively active and dominant negative RhoA constructs were kindly provided by Dr. G. Tigyi (University of Tennessee, Memphis, USA). The three cell lines used included a mocktransfected cell line, and constitutively active RhoA (V14GRhoA) cell line, and a dominant negative RhoA (N19TRhoA) cell line. Transfected PC12 cell lines were maintained in the growth medium containing 400 mg/L G418. For cell differentiation experiments, cells were plated on appropriate substrates in DMEM with 1% fetal bovine serum and 100 ng/ml nerve growth factor. For experiments on mixed substrata (laminin/MAG or laminin/myelin), PC12 were plated in DMEM with 1% lipid free-BSA in the presence or the absence of 50mg/ml of an irrelevant antibody or of a purified function blocking antibody (clone 3A3) against the rat a1b1 integrin (a gift of S. Carbonetto). PC 12 cell differentiation experiments were done in 96-well plates in duplicate, and each experiment was repeated a minimum of three times.

To culture cerebellar granule cells, 3–4 rats from P3 to P7 were decapitated. The cerebellum was removed and placed in MEM-HEPES where underlying tissue and the meninges was removed. The cerebellum was cut into small pieces and treated with 0.125% trypsin in MEM-HEPES for 20' at 37 C. The tissue was then triturated with a fire polished pasteur pipette to break up any clumps of tissue. The cells were spun down at 1500 rpm for 10', and the pellet was resuspended in MEM-HEPES with 2mM EDTA. The cell suspension was placed on an isoosmotic percoll gradient with 60% and 35% percoll, centrifuged for 15' at 2300 rpm, and the interface between the 60% and 35% percoll was collected. Cells were washed once, and resuspended in DMEM with 10% FB S, vitamins, and penicillin/streptomycin in the presence or absence of 20 mg/ml C3 transferase. Cells were placed in 4-chamber, chamber slides coated with poly-1-lysine or laminin and treated with spots of MAG or myelin. 200,00 cells per chamber were plated.

Preparation of Growth Substrates

Poly-1-lysine was obtained from Sigma (St. Louis, Mo.). Laminin was prepared from EHS tumors (Paulsson and Lindblom (1994) Cell biology: A laboratory handbook, Academic Press, pp 589–594) and collagen from rat tails (Greene, et al., (1987) *Meth. Enzymology* 147, 207–216). Myelin was made from bovine brain corpus callosum, and native MAG was purified from myelin after extraction in 1% octylglucoside and separation by ion exchange chromatography (McKerracher, L., et al., (1994) *Neuron* 13, 805–811). This native MAG has some additional proteins, including some tenascin (Xiao, Z., et al., (1997) *Neurosci. Abstr*. 23, 1994). Recombinant MAG was made in baculovirus as described (McKerracher, L., et al., (1994) *Neuron* 13, 805–811).

Test substrate were prepared as uniform substrates in 96-well plates or 4-chambered slides, or as spots on 18mm glass coverslips. First, poly-L-lysine was coated by incubation of 100 mg/ml for 3 hours at 37 C, and the wells or coverslips were washed with water and dried. Laminin substrates were prepared by incubating 25 mg/ml laminin on poly-L-lysine coated dishes for 3 hours at 37 C. Solid MAG or myelin substrates were prepared by drying down MAG overnight, or incubating at 10 mg/ml myelin solution for 3 hours on polylysine coated substrates. For 96-well plates, 1–4 mg of either recombinant MAG (rMAG) or of native MAG per well was used. For mixed laminin/myelin or laminin/MAG substrata, 8mg of inhibitory proteins and 10 mg of laminin were dried down on 96-well plates precoated with polylysine. For 4-chambered chamber slides, 40 mg MAG per chamber used, and for 100 mm plates 0.6–1 mg of MAG was dried down. Spots of MAG on coverslips were generated by plating of 2 mg/ml recombinant MAG on polylysine for 3–4 hours in a humid chamber at 37° C. Collagen substrates were made by incubating 10–15 mg/ml of rat tail collagen for 3 hours at 37° C.

Immunocytochemistry

PC 12 cells were visualized by phase contrast microscopy, or following labeling with the lipophilic fluorescent dye, DiI (McKerracher, L., et al., (1994) Neuron 13, 805–811). Granule cells were visualized by immunocyteochemistry. Following 12–24 hours in culture, cells were fixed for 30' at room temperature in 4% paraformaldehyde, 0.5% glutaraldehyde, 0.1 M phosphate buffer. Following fixation, cells were washed 3×5' with PBS and then blocked for 1 hour at room temperature in 3% BSA, 0.1% Triton-X 100. Granule cell cultures were incubated overnight with a polyclonal anti-rMAG antibody (called 57A++) to label MAG spots. The MAG antibody was detected using an FITC conjugated secondary antibody. Rhodamine conjugated phalloidin was diluted 1:200 with the secondary antibody to label granule cell actin filaments.

C3 Transferase Preparation and Use

The plasmid pGEX2T-C3 coding for the GST-C3 fusion protein was obtained from A. Hall (London). Recombinant C3 was purified as described by Dillon and Feig (Met. Enzymology, (1994), 256, pp 174–184). After fusion protein cleavage by thrombin, thrombin was removed by incubating the protein solution 1 hour on ice with 100 ml of paminobenzamidine agarose-beads (Sigma). The C3 solution was desalted on PD10 column (Pharmacia) with PBS, and sterilized through a 0.22mm filter. The C3 concentration was evaluated by Lowry assay (DC protein assay, Bio-Rad) and toxin purity was controlled by SDS-PAGE analysis.

To test the effect of C3 on the outgrowth on PC 12 cells, C3 transferase was scrape loaded into the cells before plating on appropriate substrates. Cells were grown to confluence in serum containing media in 6 well plates. Cells were washed once with scraping buffer (1 14 mM KCl, 15 mM NaCl, 5.5 mM $MgCl_2$,10 mM Tris-HCl). Cells were then scraped with a rubber policeman into 0.5 ml scraping buffer in the presence or absence of 20 mg/ml C3 transferase. The cells were pelleted, and resuspended in 2 ml DMEM, 1% FBS, and 50 ng/ml nerve growth factor before plating. 10 mg/ml C3 was added to scrape loaded cells. Cells were differentiated for 48 hours then fixed in 4% paraformaldehyde, 0.5% glutaraldehyde, 0.1 M $PO_4$ buffer.

Membrane Translocation Assay for RhoA

PC12 cells were collected and resuspended in DMEM, 0.1% BSA, 50ng/ml NGF, then plated on 100 mm dishes coated with collagen or MAG, or left in suspension. Two hours later, cells were washed with ice cold PBS+ protease inhibitors (1 mg/ml aprotinin, 1 mg/ml leupeptin, 1 mg/ml antipain, 1 mg/ml pepstatin). Cells were then scraped into 5 ml PBS+ protease inhibitors, and the cells were pelleted and washed with PBS+ protease inhibitors. The cell pellets were mechanically homogenized by 25 strokes in a glass-teflon homogenizer, the homogenate centrifuged for 20 min at 8,000 rpm, and the cell debris in the pellet was discarded. The supernatant was centrifuged for 1 hour at 100,000× g to separate members and cytosolic fractions. Membrane pellets were washed 1× with PBS+ protease inhibitors and resuspended in PBS with 0.5% SDS, and 50–100 mg of membrane protein was analyzed by SDS-PAGE on 12% gels. Gels were transferred to Protran nitrocellulose membrane and stained with Ponceau S. Blots were blocked for 1 hour in 5% skim milk in TBS, and probed overnight with Rho A antibody diluted 1:200 in 1.5% skim milk TBS. Rho A antibody was detected by using an alkaline phosphatase conjugated secondary antibody and an alkaline phosphatase detection kit (Gibco-BRL).

Growth Inhibition of PC12 Cells and Its Modulation by NGF and Laminin

PC12 cells typically extend neurites in response to NGF, but when plated on myelin substrates the cells remain round and do not extend neurites (Moskowitz, P. F., et al., (1997) J. Neurosi. Rec. 34, 129–134.) (FIG. 2). MAG is a potent inhibitor of axon growth present in myelin. We observed that PC 12 cells plated on substrates of MAG also remained rounded (FIG. 1), a finding in contrast to a report that PC12 cells are not responsive to MAG (Bartsch, U., et al., (1995) Neuron 15, 1375–1381). To further examine the response of PC12 cells to MAG, we plated three different lines of PC 12 cells on both native and recombinant MAG substrates in the presence of NGF. All of the lines of PC12 cells showed reduced cell spreading, and most cells remained rounded without neurites. However, with increasing time, some neurites were able to extend on MAG substrates (see below). We also observed that different preparations of MAG can differ in their potency to inhibit neurite growth, and that the activity of MAG is reduced or lost upon freeze-thaw.

Laminin is known to override completely, growth inhibition of NG108 cells by myelin (David, S., et al., (1995) J. Neurosci. Res. 42, 594–602). Similarly, we found that PC12 cells are able to extend neurites on mixed myelin and laminin substrates or on mixed laminin/MAG substrates (FIG. 2). To determine if signaling through integrins is responsible for overriding growth inhibition by myelin, we used the integrin function blocking antibody 3A3 raised against the a 1 subunit extracellular domain. Previous studies have documented that α1β1 integrin is the dominant integrin expressed by PC 12 cells, and that the 3A3 antibody blocks PC12 cell neurite growth on laminin (Tomaselli, K. J., et al., (1990) Neuron 5, 651–662). We plated PC12 cells on mixed myelin and laminin substrates, in the presence of the 3A3 antibody, or with a non-specific IgG antibody as a control. The 3A3 antibody blocked neurite extension on both and laminin and the mixed myelin/laminin substrates (FIG. 2). On MAG or on myelin substrates the cells remained rounded. The observation that the 3A3 antibody restores growth inhibition on mixed substrates demonstrates that laminin does not override growth inhibition by masking the inhibitory domain of MAG, but that signals elicited through integrins receptors are responsible.

Effect of C3 Transferase on PC12 cells

To investigate possible intracellular targets that may override growth inhibition by myelin and by MAG, we focused on the small GTPase Rho which is known to play a role in convergent signaling pathways that affect morphology and motility (Hall, A., (1996) *Ann. Rev. Cell Biol.* 10, 31–54). We inactivated Rho in PC12 cells by scrape loading them with the bacterial toxin C3 before plating the cells on the test substrates. C3 is known to inactivate Rho through ADP ribosylation (Udagawa, T. and McIntyre, B. W. (1996) *J. Biol. Chem.* 271, 12542–12548). On control substrates of polylysine and laminin, treatment with C3 potentiated both the number of cells with neurites and the length of neurites from cells (FIG. 3). On MAG and myelin substrates where neurite formation is inhibited, C3 has a dramatic effect on the ability to extend neurites (FIG. 3). When treated with C3, about half of the PC12 cells plated on either rMAG or native MAG has neurites of approximately 1 cell body diameter. In contrast, the untreated cells remained rounded and clumped. Similarly, PC12 cells plated on myelin remained rounded, but the addition of C3 allowed neurites to extend directly on the myelin substrate. These results demonstrate that C3 treatment elicits neurite growth from PC12 cells plated on growth inhibitory myelin or MAG substrates.

Growth of Dominant-Negative Rho-Transfected Cells on MAG Substrates

PC 12 cells transfected with constitutively active RhoA (V14GRhoA), and PC 12 cells transfected with dominant negative RhoA (N19TRhoA), and the mock-transfected cells, were examined for their ability to extend neurites on different test substrates. Cells with constitutively active mutation, V14GRhoA cells, differentiated poorly on all substrates, including poly-L-lysine and laminin. The treatment of the V14GRhoA cells with C3 allowed the growth of some short neurites on all of the test substrates, including MAG.

In the same series of experiments the response of dominant negative Rho-transfected cells, N19TRhoA cells, to MAG and myelin substrates was examined. When N19TRhoA cells were plated on MAG substrates, they spread and did not remain rounded as did the mock transfected PC12 cells. A small number of cells had short neurites, an effect that was observed on both the rMAG and native MAG substrates (FIG. 3).

C3 treatment of mock transfected and N19TRhoA cells had a dramatic effect on neurite outgrowth as most cells had extensive neurites (FIG. 3). The effect of C3 on N19TRhoA cells was much more marked that the effect on the mock transfected cells. Therefore, the combination of C3 treatment and transfection of dominant negative Rho elicited excellent outgrowth of neurites from PC12 cells plated on inhibitory MAG (and myelin) substrates.

Effect of C3 on Primary Cells

To test the involvement of Rho in the response of primary neurons to MAG and to myelin substrates, cerebellar granule neurons were plated on test substrates and treated with C3. Neurite outgrowth from these cells was known to be inhibited by MAG (Li, M., et al., (1996) *J. Neurosic. Res.* 46, 404–414) and the C3 sitmulated growth of neurites from the granule cells on both permissive and inhibitory substrates.

The Growth Substrate Influences the Cellular Location of Rho

Figure 4:
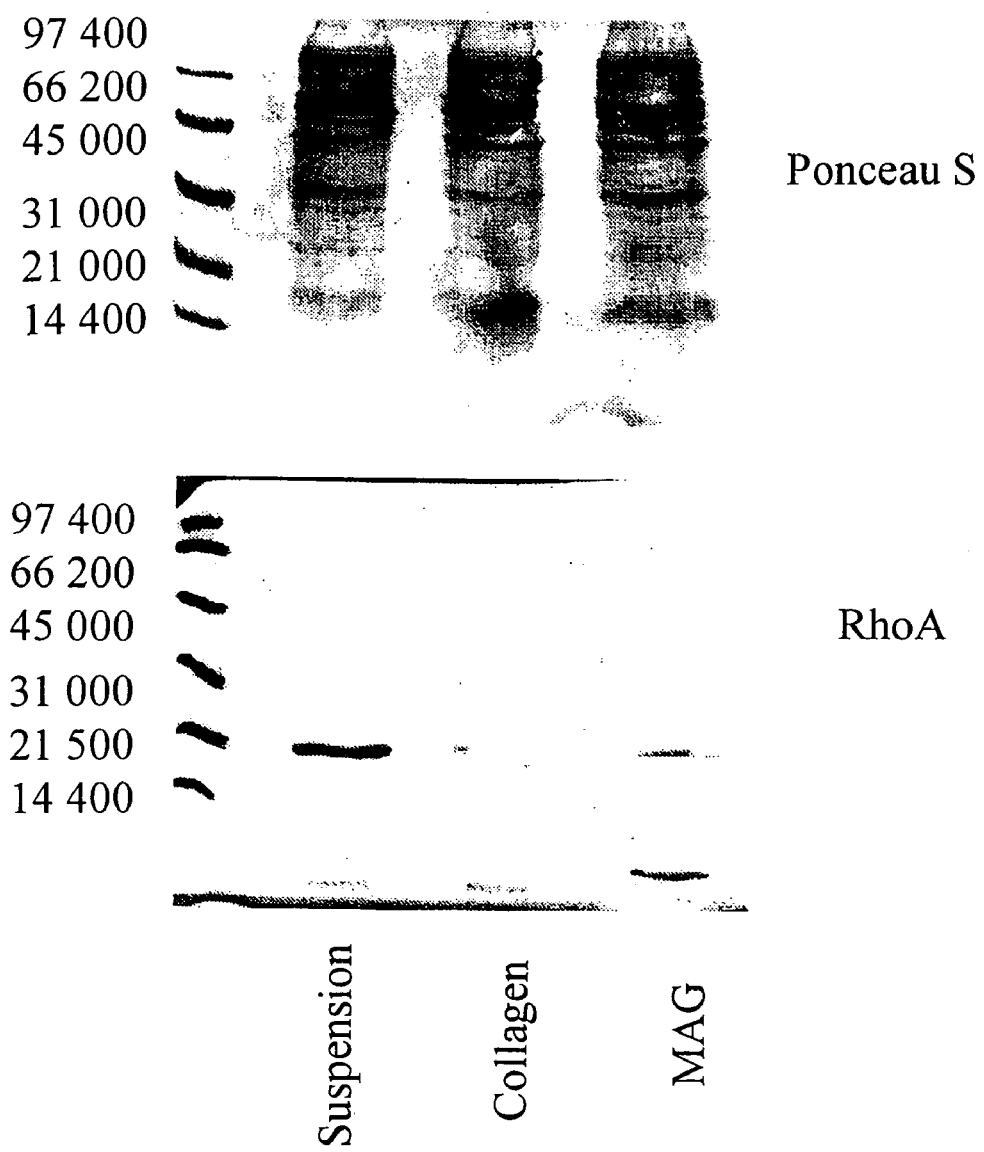
FIG. 4 shows activation of Rho on MAG substrates. Activated Rho is associated with the plasma membrane. To determine if activated Rho was detected under conditions where PC12 cells do not grow neurites, cells were grown in suspension or plated on MAG or collagen substrates. Two hours later the plasma membranes were purified, the proteins separated by SDS PAGE, and the proteins transferred to nitrocellulose and stained with Ponceau S (toP panel). Rho A was detected on the blots by immunoreactivity with anti-RhoA antibody (bottom panel). Immunoreactivity was strongest when cells were grown in suspension or when cells were plated on MAG. Therefore, Rho A is more active when cells are kept in suspension or plated on MAG than when plated on growth-permissive collagen.

Rho is associated with the plasma membrane when it is in an activated state, and it moves into the cytosolic fraction when it is in the GDP-bound inactive state. To determine if the growth substrate influences the cellular localization of Rho, cells were either left in suspension or plated on MAG or collagen substrates, and prepared membranes from the cells two hours later. It was shown that Rho was principally localized in the cytosolic fraction when cells were plated on collagen, a growth permissive substrate. However, Rho was associated with the plasma membrane when cells where grown in suspension and when cells were plated on MAG (FIG. 4).

Example II

In Vivo Demonstrations

1. Effect of C3 on Cultured Retinal Neurons

Figure 5A:
FIG. 5 shows treatment of retinal neurons with C3 stimulates neurite growth on polylysine and MAG substrates. On nMAG substrates neurite growth is inhibited (FIG. 5A), but after C3 treatment retinal neurons plated nMAG substrates extend neurites (FIG. 5B). Growth of neurites from retinal neurons plated on PLL (FIG. 5C). Bar, 50 µm.
Figure 5B:
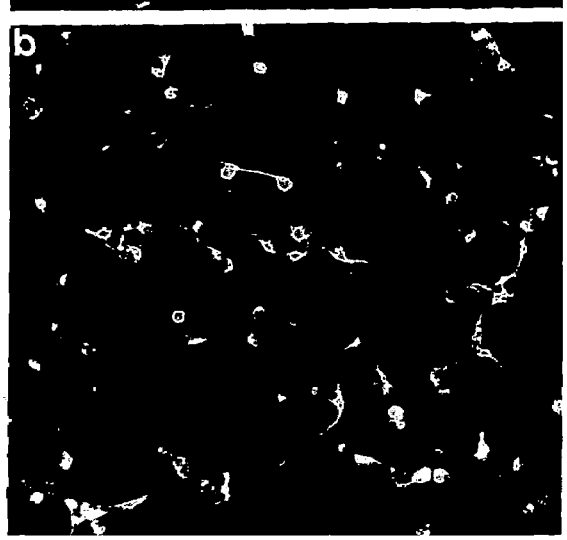
Figure 5C:
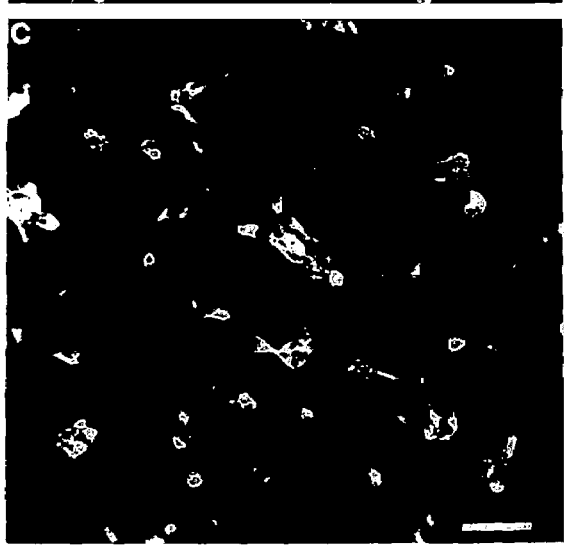

To test the involvement of Rho in the response of primary neurons to MAG and to myelin substrates, we purified retinal neurons and treated them with C3. Neurite outgrowth from these cells was inhibited by MAG (FIG. 5a). As with PC12 cells, treatment of retinal neurons cells with C3 allowed neurite extension on the growth inhibitory MAG substrates to an extent similar to that observed on control substrates (FIG. 5b and 5).

Figure 6:
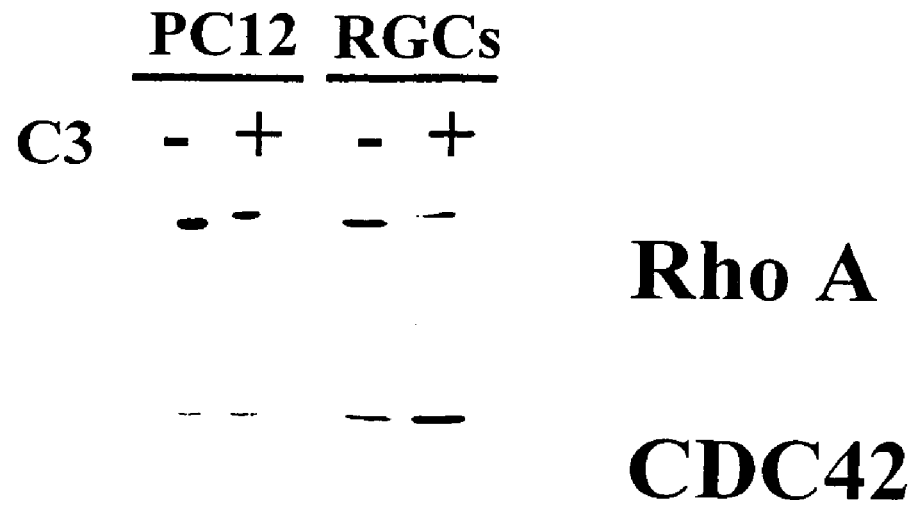

To ensure that the effect of C3 treatment resulted from uptake of C3 into the cells, we examined by Western blot the electrophoretic mobility of Rho in PC 12 cells and retinal neurons treated with C3 (FIG. 6). It has previously been shown that ADP-ribosylation of Rho results in decreased mobility of Rho on SDS-acrylamide gels (Method Enzymol. Vol. 256, Chapter 22 pg. 198). For our experiments, PC12 cells were scrape-loaded with C3 or with scrape-loading buffer as a control, and cells lysates were prepared after 48 hours in culture. Western blots of the lysates with anti-RhoA antibody revealed an increase in the apparent molecular weight in cells treated with C3. As a control for the specificity of the effect, we probed the same blots for another small GTPase of the Rho family, Cdc42. Cdc42 did not show any change in mobility upon treatment with C3. To culture retinal neurons, retinas were removed from P1–P5 rat pups, and the cells were dissociated with 12.5 U papain/ml in Hanks balanced salts solution, 0.2 mg/ml DL cysteine and 20 I g/ml bovine serum albumin. The dissociated cells were plated on test substrates in the presence of 50 mg/ml BDNF in DMEM with 10% FBS, vitamins, and penicillin/streptomycin in the presence or absence of 50 mg/ml C3 transferase. Neurons were visualized by fluorescent microscopy with anti-β III tubulin antibody.

2. Effects of C3 on Retinal Ganglion Cell Axon Growth In Vivo

To explore the possibility that treatment of damaged axons with C3 might foster regeneration in vivo, we examined regeneration of retinal ganglion cell (RGC) axons in the optic nerve 2 weeks after optic nerve crush. Recently, it has been shown that microlesions in the CNS reduce the extent of the glial scar and allow axons access to CNS white matter distal to the lesion (Davies, S. J. A., et al. (1997) *Nature* 390, 680–683). To make microlesions of optic nerve, 10.0 sutures were used to axotomize RGC axons by constriction (FIG. 7A). Retrograde labeling of RGCs from the superior colliculus (not shown), as well as anterograde labeling techniques (eg., FIG. 7A) verified that RGC axons were effectively axotomized. To apply C3 to crushed nerves, Gelfoam soaked with 2 mg/ml C3 was wrapped around the left optic nerve at the crush site, and two Elvax tubes, each loaded with 20 mg of C3, were positioned for sustained slow release (FIG. 7A). Twelve animals were treated with C3 and a further 8 animals were treated with PBS as controls. Crushed and regenerating axons were visualized by anterograde labeling with cholera toxin injected into the eye 12 days after optic nerve crush (FIG. 7A). Fourteen days after optic nerve crush, longitudinal cryostat sections of the optic nerves were examined by fluorescent microscopy for immunoreactivity to cholera toxin to detect anterogradely labeled RGC axons.

Figure 7B:
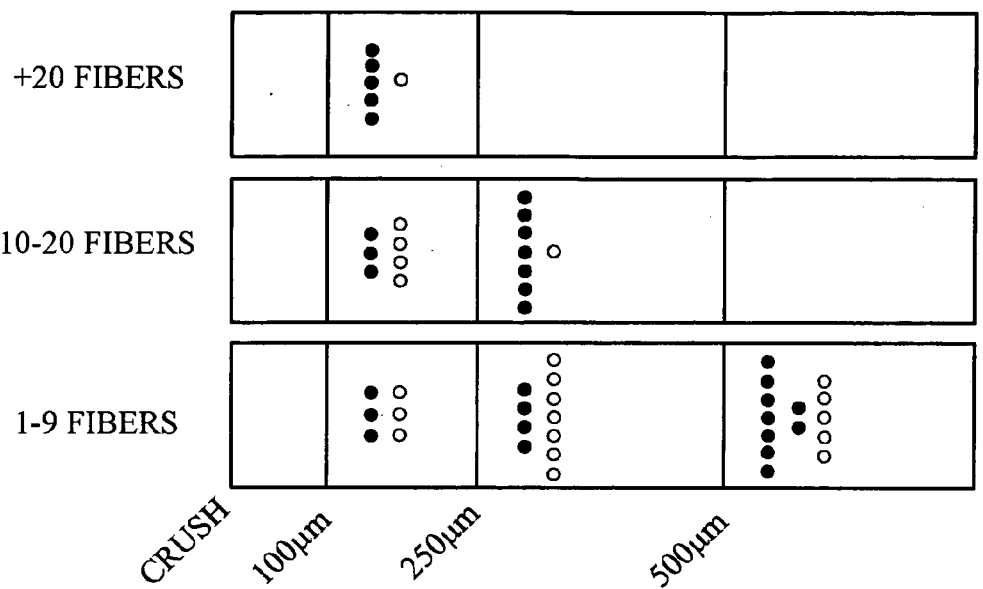
FIG. 7B shows quantitation of axon regeneration across the site of lesion. Representation of regeneration observed in different animals. For each animal, the maximum number of axons observed in a single 14 µm section was counted at different distances from the site of the crush. Each point represents one animal, but animals with growth past 500 µm are also represented at the shorter distances. Large umbers of regenerating fbers (>10/section) were observed to cross the lesion after C3 treatment compared to treatment with PBS.
Figure 7C:
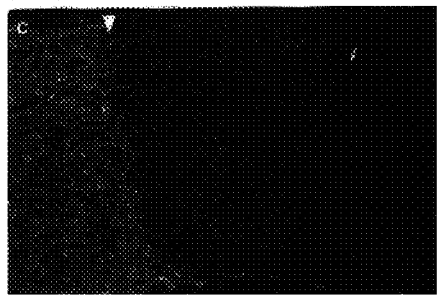
FIG. 7c, 7d, 7e, and 7C–F show treatment of crushed optic nerve with C3 stimulates regenerative growth of retinal ganglion cells axons.

In control optic nerves that received optic nerve crush alone, no RGC axons extended past the crush site (n=3 animals). In control animals treated with PBS-Elvax pellets and gelfoam, the crush site was easily detected where most anterogradely labeled axons stopped abruptly (FIG. 7C). However, in these animals, a few axons did extend past the crush (FIG. 7C, arrows), and the numbers of axons that regenerated varied from animal to animal. The application of Gelfoam and Elvax tubes may have altered the response to injury. Nonetheless, the response to C3 treatment applied with this lesion paradigm was dramatic.

Figure 7D:
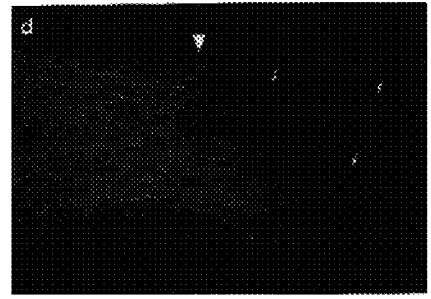
Figure 7E:
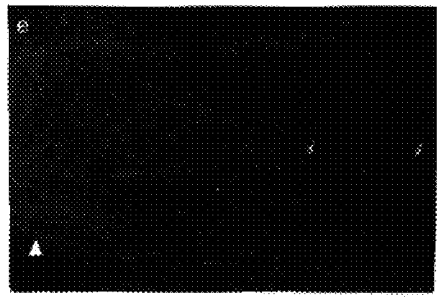
Figure 7F:
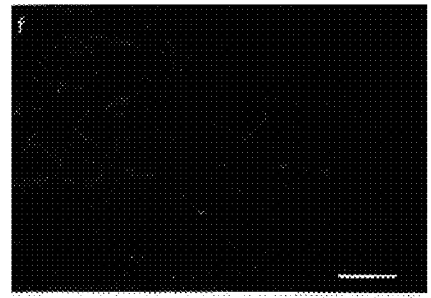

We observed that C3 treatment allowed many RGC axons to grow past the region of the lesion. In 7 of 12 C3-treated animals, the lesion site was not clearly defined because of the large numbers of axons that extended through the site (FIG. 7D and E). Many of the axons that extended past the lesion site showed a twist path of growth, supporting their identification as regenerating axons (FIG. 7f) A quantitative comparison of C3 and PBS treated animals revealed that more fibers grew past the lesion site after C3 treatment than after PBS treatment (FIG. 7B). For this analysis we made a conservative estimate of the lesion site based on morphology, and counted the number of fibers in the distal optic nerve in 14 μm sections. Seven of 12 C3-treated animals showed at least one section with 10–20 axons extending 250 μm past the crush, compared with 1 of 8 of the PBS-treated controls (FIG. 7). In some animals regenerating axons were observed up to 1 mm from the crush, an extent of regeneration similar to that observed in mouse optic nerve after treatment with IN-i antibody to block myelin inhibitors where fibers extended up to 750 μm (Bartsch, U., et al., (1995) *Neuron* 15, 1375–1381).

C3 Treatment of Crushed Optic Nerve in Adult Rats

Rats were anesthetized with 0.6 ml/kg hypnorm, 2.5 mg/kg diazepan and 35 mg/kg ketamin. The left optic nerve was exposed by a supraorbital approach, the optic nerve sheath slit longitudinally, the optic nerve lifted out and crushed 1 mm from the globe by constriction with a 10.0 suture held for 60 seconds (FIG. 7A). For C3 treatment and buffer controls, Gelfoam soaked in PBS or 2 mg/ml C3 transferase was placed on the nerve at the lesion site. Two 3 mm long tubes of Elvax (Sefton, et al., (1984)) loaded with buffer or 20 mg C3 were inserted in the Gelfoam near the nerve for continued slow release of C3 (FIG. 2A). Twelve days after crush, 5 ml of 1% cholera toxin β subunit (List Biological laboratories, Inc., Cambell, Calif.) was injected into the vitreous to anterogradely label retinal ganglion cell axons (FIG. 7A). Two weeks after optic nerve crush the animals were fixed by perfusion with 4% paraformaldehyde, and the eye with attached optic nerve was removed and postfixed in 4% paraformaldehyde. Longitudinal cryostat sections were processed for immunoreactivity to cholera toxin with goat anti-cholera toxin at 1:12,000 (List Biol. Labs Inc., CA) followed by rabbit anti-goat biotinylated antibody (1:200, Vector Labs, Burlingame, Calif.), and DTAF-streptavidin (1:500, Jackson Immunoresearch Laboratories).

Discussion

Here we report that the small GTP binding protein Rho is likely to be a key intermediate in the neuronal response to neurite growth inhibitory signals. Treatment of cultured PC12 cells, retinal neurons, and cerebellar granule cells with C3 enzyme to inactivate Rho allowed neurites to extend directly on inhibitor substrates of MAG or myelin. Also, PC12 cells transfected with dominant negative RhoA extended neurites on MAG substrates. Therefore, inactivation of Rho was sufficient to allow neurite growth on MAG or myelin substrates when neurons were grown in the presence of neurotrophic factors.

Further, our observations of microlesioned optic nerves after treatment with C3 provide the first evidence that the inactivation of Rho in axons and non-neuronal cells near the site of lesion can help foster regeneration after injury. While the in vitro experiments showed that C3 can affect directly the growth of neurites from retinal cells, it is likely that the effects we observed after application of C3 to the optic nerve in vivo are more complex. C3 may affect other non-neuronal cells, such as macrophages and astrocytes, and these possibilities need to be further examined. Nonetheless, our data provide compelling evidence that C3 can promote neurite growth on inhibitory substrates in vitro, and helps to overcome growth inhibition in vivo.

Regulation of Neurite Growth by Rho Family Members

Not all of the myelin-derived inhibitory molecules are known to date, and less is known about the neuronal receptors for growth inhibitory molecules. Several different MAG receptors have been identified (Collins et al., 1997; Yang et al., 1996), and additional neuronal receptors to myelin inhibitors are likely to exist. Targeting intracellular signaling mechanisms converging to Rho rather than individual receptors may be the most practical way to overcome growth inhibition in vivo. The advantage of inactivating Rho to stimulate regeneration is that axons can regenerate directly on the native terrain of the CNS, and thus may be more likely to find their natural targets.

Both MAG and other myelin-derived growth inhibitory proteins block axon extension by causing growth cone collapse (Li, M., et al., (1996) *J. Neurosci. Res.* 46, 404–414; Bandtlow, C. E., et al., (1993) *Science* 259, 80–83). These findings suggested to us that growth cone collapse by the myelin-derived inhibitors might be regulated by Rho. Moreover, in non-neuronal cells, Rho participates in integrin-dependent signaling (Laudanna, C., et al., (1996) *Science* 271, 981–983; Udagawa, T. and McIntyre, B. W. (1996) *J. Biol. Chem.* 271, 12542–12548). Together with the observation that laminin can override myelin-derived inhibition, we hypothesized that small GTPases of the Rho family might play a role in integrating singaling from positive and negative growth cues. To investigate this possibility, we have made use of the ADP-ribosyl transferase C3 from Clostridium botulinum that efficiently inactivates Rho without affecting Rac and Cdc42, two other members of the Rho family (Udagawa, T. and McIntyre, B. W. (1996) *J. Biol. Chem.* 271, 12542–12548) and found that C3 treatment fosters neurite growth in the presence of growth inhibitors. Moreover, immunocytochemical observations indicate that Rho protein is concentrated at the filopodial tips of growth cones in adhesion structures called point contacts (Renaudin et al., 1998). Therefore, our in vitro results suggest the Rho signaling pathway is a key target for regulating growth cone motility and stimulating regeneration.

Moreover, this data is relevant to the finding of Song et al. (Song et al., *Science* 281: 1515–1518 (1998)) who report that growth cone repulsion by MAG can be converted into attraction by elevation of intracellular cAMP levels to activate protein kinase A (PKA). Experiments with non-neuronal cells has implicated cAMP in the regulation of Rho because elevation of cAMP inhibits Rho activation (Laudanna, C., et al., (1996) *Science* 271, 981–983). In PKA deficient PC 12 cells, elevation of cAMP fails to protect from the activation of Rho by lysophosphatidic acid (Tigyi, G., et al., (1996) *J. Neurochem*. 66, 537–548), a finding that suggests that PKA-dependent regulation of Rho occurs in neural cells as well. Therefore, the cAMP-dependent regulation is likely to be upstream of Rho (Laudanna, C., et al., (1996) *Science* 271, 981–983).

The Non-Neuronal Response to Optic Nerve Injury

Remarkably, we observed that RGC axons crossed the lesion site to enter the distal optic nerve after treatment of injured optic nerve with C3. Some axons grew up to 1 mm past the site of lesion. This distance is comparable to the maximal distances observed following treatment of optic nerve with IN-1 antibody (Bartsch, U., et al., (1995) *Neuron* 15, 1375–1381). The most striking feature of our results was the large number of axons that were able to cross the lesion site compared to PBS-treated controls (see FIG. 7). Therefore, it is appears that C3 was also able to promote axon growth on inhibitory proteins present at the glial scar, indicating that targeting the Rho signaling pathway as widespread efficacy in stimulating axon regeneration after injury.

Example III

Inactivation of Rho or ROK Promotes Growth on Primary Neurons Plated on Complex Inhibitory Substrates We tested if treatment of primary neurons with C3 or with Y27632 (Y-27632) was sufficient to stimulate growth on complex inhibitory substrates typical of the glial scar and white matter. In this particular experiment, primary retinal neurons were isolated from PO-P3 rats as described (Lehmann et al., J Neurosci 19:7537–47, 1999). Test substrates were plated in 8-well chamber slides coated with 25 µg/ml poly-L-lysine. Myelin substrates were made by coating with 8 µg purified bovine brain myelin dried overnight at room temperature. Chondroitin sulfate proteoglycan (CSPG) substrates were made by incubating 0.5 µg/ml mixed proteoglycans (Chemicon International, Inc. Temecula, California) overnight in poly-L-lysine -coated chamber slides. Dissociated cells were washed, triturated with 25 or 50 µg/ml C3 or buffer, or with 35, 3.5 or 0.35 µM Y27632, and plated in culture medium with 50 ng/ml brain derived neurotrophic factor (BDNF) with or without C3 or Y27632. After 2 days, the plates were fixed with 4% paraformaldehyde, 0.5% gluteraldehyde, and neurons were identified by immunocytochemistry using a 62 III tubulin antibody (Sigma, Oakville, Canada). Example of preparation of Y27632 has been disclosed in U.S. Pat. No. 4,997,834 (Muro et al.,).

Figure 8:
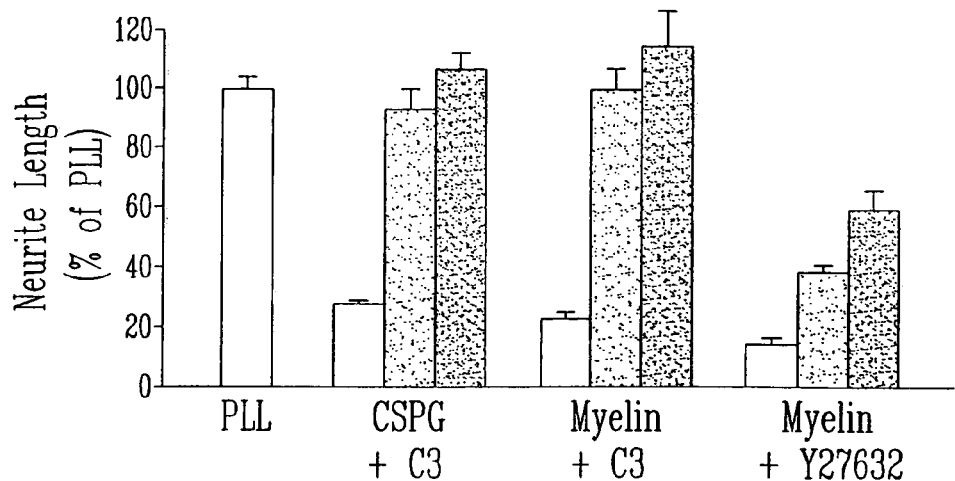
FIG. 8 shows the effect of Y27632 on neurite outgrowth of primary neurons plated on ihibitory substrates compared with c3. P0 retinal ganglion cells (RGCs) were examied after 48 hours on the following test substrates: Ploylysine (PLL) chondroitin sulfate proteoglycan (CSPG) or myeli in the presence or absence of c3 or Y27632. Shown in the average RGC neurite length after treatment with 50 µg/ml C3 or Y27632 (dense hatchig), 25 µg/ml C3 or Y27632 (light hatchig), or no treatment (white).

Neurons plated on chondroitin sulfate proteoglycans (CSPG) or purified myelin had a rounded shape. After treatment with C3 or Y27632, neurons plated on complex inhibitory substrates were able to extend neurites. Treatment either with C3 or Y27632 significantly increased the length of neurites compared to untreated cells plated on myelin or CSPG. These results demonstrate that inactivation of Rho or inhibition of ROK stimulates retinal neurons to extend neurites on growth inhibitory substrates. These results, illustrated in FIG. 8, were analyzed quantitatively by measuring the average of retinal ganglion cells neurite length of the longest neurite per cell after 48 hours on PLL, CSPG or myelin including C3 or Y27632.

Treatment of Injured Spinal Cord Promotes Long Distance Regeneration

Balb-c female mice (n=70) of approximately 20 g were anaesthetized with 0.4 ml/kg hypnorm and 5 mg/kg diazepam. A segment of the thoracic spinal cord was exposed using fine rongeurs to remove the bone, and a dorsal over-hemisection was made at T7. Fine scissors were used to cut the dorsal part of the spinal cord, which was cut a second time with a fine knife to ensure the lesion extended past the central canal. A fibrin adhesive delivery system was prepared using a Tisseel VH kit (ImmunoAG, Vienna, Austria). According to manufacturer's instructions for slow polymerization, lyophilized fibrinogen was reconstituted in an aprotinin solution, thrombin was reconstituted in a calcium chloride solution, and both solutions were warmed to 37° C. C3 (40 µg) or Y27632 (50 µg) was added to 25 µl of the thrombin solution. This was mixed with 25 µl of the fibrinogen solution just before application to the spinal cord to allow infiltration of the mixture into the lesion site before polymerization. In some animals, 10 µl of the 1 mg/ml C3 solution was added directly to the lesion site before injection of the C320 containing fibrin adhesive. As controls, a second group of animals received fibrin adhesive alone after injury, and a third group was left untreated. Collagen gels with C3 were formed as follows.

C3 was lyophilized (40 µg per mouse) then reconstituted in 10 ml of 7.5% $NaHCO_3$, and then 25 ml of rat tail collagen at 0.7 mg/ml was added. Ten microliters of C3 was added to the lesion cavity before applying the C3 containing collagen gel. For retransection of the spinal cord 3 weeks after SCI, the spinal cords were cut at T6 as described above, and the animals were observed for changes in behavior by BBB testing for 1 week after the second surgery.

Anterograde labeling was performed as follows: three weeks to 3 months after injury, the corticospinal tract (CST) fibers were labeled by injection of the anterograde tracer WGA-HRP (wheat germ agglutinin-horseradish peroxidase) into the motor cortex as described (Huang et al., Neuron 24:639–647, 1999). Two days later, the animals were perfused transcardially with saline, then 4% paraformaldehyde, and the spinal cords and brains were removed. Measurement of axon regeneration was determined from serial 30 µm cryostat sections assessed independently by 2 reviewers.

Figure 9:
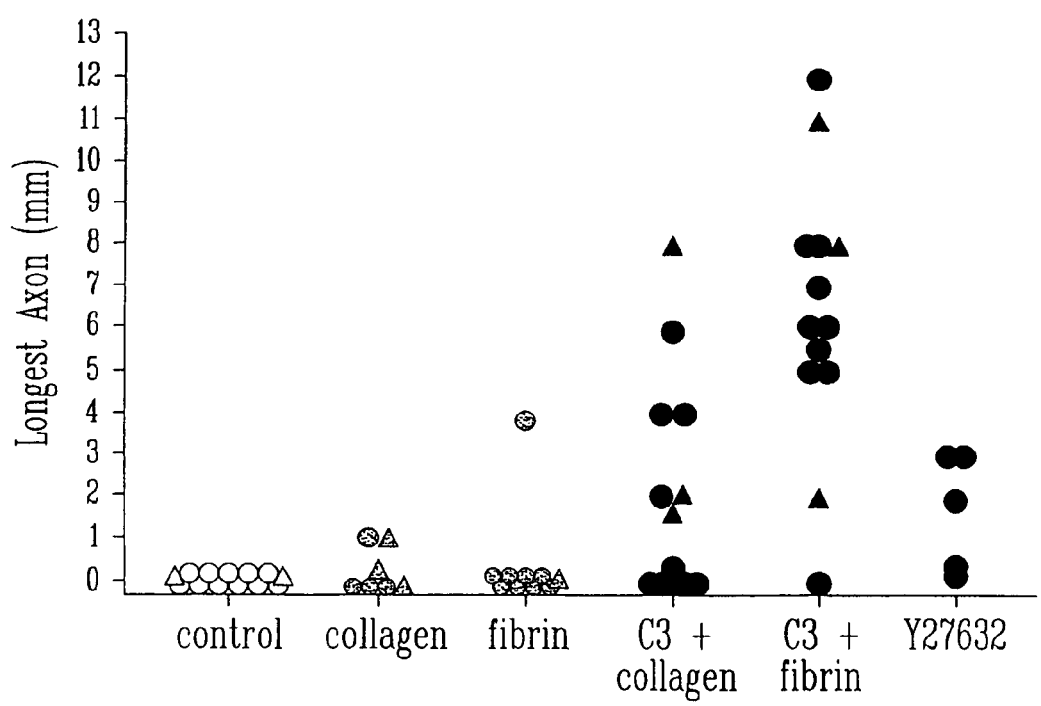
FIG. 9 shows the measurement of regeneration distances in mice with spinal cord injury alone, in mice treated with collagen and fibrin as controls, in mice animals treated with C3 in collagen or fibrin gels, and in mice treated with Y27632 in fibrin. Each point represents one animal. The circles are animals examined at 3 weeks to one month, the triangles animals examined 3 months after spinal cord injury.

To assess the potential of Rho inactivation to treat spinal cord injury (Sd), we cut the spinal cord of adult mice at T7 by a dorsal over-hemisection (Huang et al., Neuron 24:639–647, 1999). We tested local delivery of C3 in collagen (Joosten, J. Neurosci. Res. 41:481–490, 1995) or in a fibrin adhesive (Herbert, 1998) that polymerizes in vivo several seconds after injection (Herbert, J. Biomed. Mater Res. 40:551–559, 1998); Y27632 was tested in the fibrin adhesive. Anterograde tracing with WGA-HRP of corticospinal tract (CST), a tract often used to study histological regeneration, was used to assess fiber growth in six groups of animals: animals treated with fibrin plus C3 (n=13), collagen plus C3 (n=12), fibrin plus Y27632 (n=5), fibrin alone (n=10), collagen alone (n=7), and SCI with no treatment (n=13) (FIG. 9). Without C3 or Y27632 treatment, transected CST axons retracted back from the site of lesion by approximately 300 µm, although in animals treated with fibrin alone some regenerative sprouts did extend from the retracted bundle. Application of C3 to the injured spinal cord elicited extensive sprouting into the dorsal white matter and the lesion scar. Treated animals with Y27632 showed regenerative sprouting into the dorsal white matter and toward the lesion site. To assess axons distal to the lesion site, the distance of the longest axon was measured. Axons were found up to 12 mm from the lesion site in C3 treated animals and up to 3 mm from the lesion site in Y27632 treated animals (FIG. 9), while buffer-treated animals showed retraction from the lesion site. Therefore, after treatment with C3 or with Y27632, axons were found to extend past the lesion into the distal white matter. These axons have a twisted course of growth typical of regenerated axons.

Behavioral Testing

To test functional recovery after SCI and C3 or Y27632 treatment, we measured HL motor function using the Basso-Beattie-Bresnahan (BBB) locomotor rating scale (Basso et al., 1995) (n=37). Since a toe clearance phase cannot be evaluated in recuperating mice, we modified the rating to a 17 point scale. Behavioral recovery was assessed for one month after SCI in an open field environment by the BBB method (Basso et al., 1995). We modified the 21 point BBB scale to a 17 point score because mice do not exhibit differences in toe drag that can be monitored visually. Thus, scale points 16, 17 and 18 were removed from the scale. Mice raise their tail early in their recovery, and score 19 for tail up position was removed, leaving a 17 point total score. The mouse modified BBB score was as follows: [0] no observable hindlimb (HL) movement; [1] slight movement of one or two joints; [2] extensive movement of one joint and/or slight movement of one other joint; [3] extensive movement of two joints; [4] slight movement of all three joints of the HL; [5] slight movement of two joints and extensive movement of the third; [6] extensive movement of two joints and slight movement of the third [7] extensive movement of all three joints of the HL, walking with little/no weight support; [8] extensive movement of all three joints, walking with weight support; [9] frequent to consistent dorsal stepping with weight support; [10] frequent plantar stepping with weight support; [11] consistent plantar stepping with weight support, no coordination; [12] consistent plantar stepping with consistent weight support, occasional forelimb-hindlimb (FL-HL) coordination; [13] consistent plantar stepping with consistent weight support, frequent FL-HL coordination; [14] consistent plantar stepping with consistent weight support, consistent FL-HL coordination; predominant paw position during locomotion is rotated internally or externally, or consistent FL-HL coordination with occasional dorsal stepping; [15] consistent plantar stepping with consistent weight support, consistent FL-HL coordination; predominant paw position is parallel to the body; frequent to consistent curled toes, trunk instability; [16] consistent plantar stepping with consistent weight support, consistent FL-HL coordination; predominant paw position is parallel to the body, flat toes, some trunk instability; [17] consistent plantar stepping with consistent weight support, consistent FL-HL coordination; predominant paw position is parallel to the body, flat toes and consistent stability in the locomotion. For scoring, each animal was videotaped for 3 minutes and 2 reviewers participated. In the late phase of recovery, the BBB score was determined from sequences of 4 steps or more from digitized videos projected on a computer screen at ¼ speed.

Figure 10:
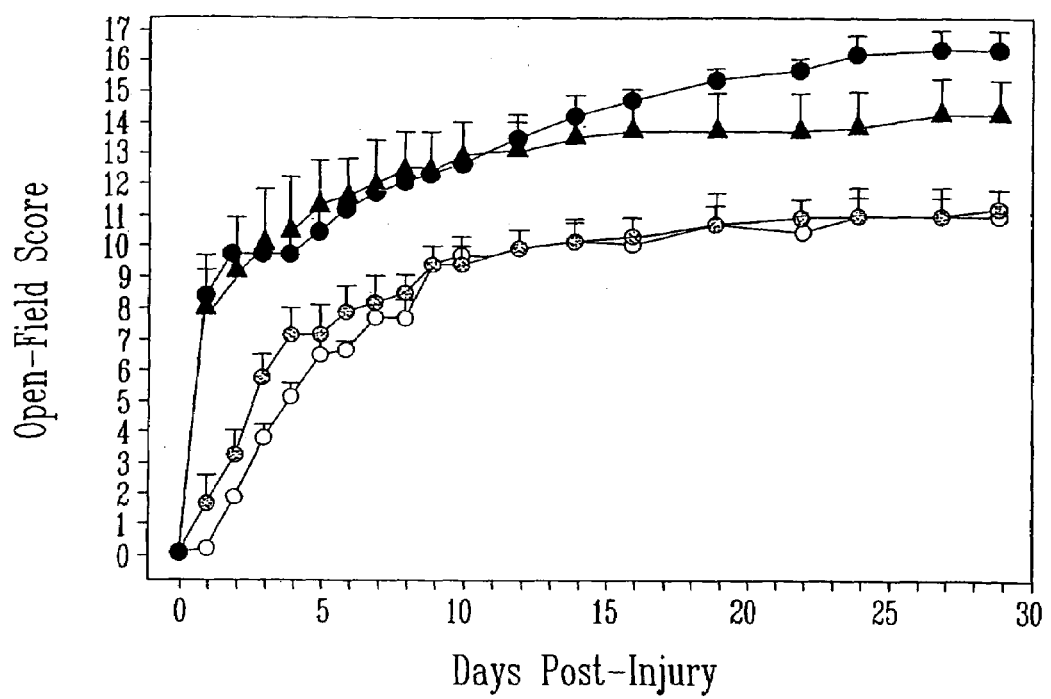
FIG. 10 shows an analysis of functional recovery. Modified BBB scores of C3-treated (black circles), Y27632-treated (black triangles), fibrin-treated (hatched circles), and untreated (open circles) mice to evaluate recovery of locomotion for one month following dorsal over-hemisection. Each point represents the average of 10–11 animals SEM for controls and C3 experiments, or 5 animals for Y27632.

Twenty-four hours after surgery, control mice were paraplegic (FIG. 10) and moved by pulling themselves forward with their forelimbs. Mice treated with C3 or with Y27632 showed a remarkable recovery within 24 hours (FIG. 10), already walking with weight support (FIG. 10). While this early recovery is too rapid to be explained by long distance regeneration, possible mechanisms include local reorganization of central pattern generator circuitry (Ribotta et al., J Neurosci 20:5144–52, 2000), pharmacological activation of neurotransmitter receptors (Rossignol et al., Humana Press, Totowa. 57–87, 2000) or neuroprotection (Laufs et al., J Clin Invest 106:15–24, 2000; Trapp Ct al., Mol Cell Neurosci 17:883–94, 2001). Mice that had received C3 or Y27632 treatment continued to recover over the 1 month period of observation, and exhibited hindlimb-forelimb coordination. By contrast, the average recovery plateau for untreated animals was limited to unstable walking without hindlimb-forelimb coordination. Retransection of the spinal cord at 3 weeks (n=8) eliminated any achieved hindlimb recovery in both C3 treated (n=5) and control (n=3) animals (data not shown).

What is claimed is:

1. A method of promoting neural growth, the method comprising delivery to a central nervous system tissue of (+)-trans-4-(1-aminoethyl)-1-(4-pyridylcarbamoyl)-cyclohexane.

2. A method of stimulating regenerative growth of damaged neuronal axons in a patient with traumatic nervous system damage, the method comprising delivering directly at a traumatic lesion site in a nerve in a patient, in an amount effective to suppress Rho family member-mediated inhibition of neuronal axon growth, a Rho family antagonist that antagonizes Rho-associated kinase activity, wherein the antagonist is (+)-trans-4-(1-aminoethyl)-1-(4-pyridylcarbamoyl)-cyclohexane.

3. The method of claim 2, wherein the regenerative growth comprises a twisted path of growth past the lesion site.

4. The method of claim 2, wherein the regenerative axon growth extends distal to the lesion site.

5. The method of claim 2, wherein the regenerative axon growth is up to 3 millimeter (mm) past the lesion site.

6. The method of claim 2, wherein the nervous system damage is selected from the group consisting of a spinal cord injury, a spinal cord lesion, and a surgical nerve lesion.

7. The method of claim 2, wherein the antagonist is administered with a pharmaceutical carrier or delivery system.

8. The method of claim 7, wherein the carrier is a fibrin adhesive.

* * * * *